(12) United States Patent
Hamlyn et al.

(10) Patent No.: US 8,399,481 B2
(45) Date of Patent: Mar. 19, 2013

(54) COMPOUNDS

(75) Inventors: Richard John Hamlyn, Cambridge (GB); David Madge, Cambridge (GB); Mushtaq Mulla, Cambridge (GB); Basil Hartzoulakis, Cambridge (GB); Simon Mark Jones, Swindon (GB); Derek Edward John, Cambridge (GB); Oliver Gareth Dugdale, Cambridge (GB)

(73) Assignee: Xention Ltd, Pampisford, Cambridge (GB)

( * ) Notice: Subject to any disclaimer, the term of this patent is extended or adjusted under 35 U.S.C. 154(b) by 175 days.

(21) Appl. No.: 12/794,493

(22) Filed: Jun. 4, 2010

(65) Prior Publication Data
US 2011/0136859 A1  Jun. 9, 2011

(30) Foreign Application Priority Data
Jun. 4, 2009  (GB) .................................. 0909671.0

(51) Int. Cl.
*C07D 217/24* (2006.01)
*A61K 31/4725* (2006.01)
(52) U.S. Cl. ......... 514/309; 514/418; 546/141; 548/472
(58) Field of Classification Search .................. None
See application file for complete search history.

(56) References Cited

U.S. PATENT DOCUMENTS

| | | | |
|---|---|---|---|
| 6,077,680 | A | 6/2000 | Kem et al. |
| 6,083,986 | A | 7/2000 | Castle et al. |
| 6,194,458 | B1 | 2/2001 | Baker et al. |
| 6,300,342 | B1 | 10/2001 | Heckel et al. |
| 2011/0136860 | A1 | 6/2011 | Hamlyn et al. |

FOREIGN PATENT DOCUMENTS

| | | |
|---|---|---|
| DE | 197 27 117 A1 | 1/1999 |
| EP | 1 844 768 A1 | 10/2007 |
| WO | WO 96/40100 A1 | 12/1996 |
| WO | WO 00/25774 A1 | 5/2000 |
| WO | WO 01/40231 A1 | 6/2001 |
| WO | WO 03/082205 A2 | 10/2003 |
| WO | WO 2004/065351 A1 | 8/2004 |
| WO | WO 2005/030709 A1 | 4/2005 |
| WO | WO 2007/024944 A1 | 3/2007 |
| WO | WO 2007/056078 A2 | 5/2007 |
| WO | WO 2007/109211 A2 | 9/2007 |
| WO | WO 2007/110171 A1 | 10/2007 |
| WO | WO 2008/038053 A1 | 4/2008 |
| WO | WO 2008/113760 A2 | 9/2008 |
| WO | WO 2008/149163 A2 | 12/2008 |

OTHER PUBLICATIONS

Amos, G. et al., "Differences between outward currents of human atrial and subepicardial ventricular myocytes," *J. Physiol.*, 491:31-50, The Physiological Society, US (1996).
Armstrong, C. and Hille, B., "Voltage-Gated Ion Channels and Electrical Excitability," *Neuron*, 20:371-380m Cell Press, US (1998).
Bachmann, A. et al., "Characterization of a novel Kv1.5 channel blocker in *Xenopus oocytes*, CHO cells, human and rat cardiomyocytes," *Naunyn-Schmiedeberg's Arch. Pharmacol.*, 364:472-478, Springer, DE (2001).
Baell, J. et al., "Khellinone Derivatives as Blocker of the Voltage-Gated Potassium Channel Kv1.3: Synthesis and Immunosuppressive Activity," *J. Med. Chem.*, 47:2326-2336, American Chemical Society, US (2004).
Beeton, C. et al., "Selective Blocking of Voltage-Gated $K^+$ Channels Improves Experimental Autoimmune Encephalomyelitis and Inhibits T Cell Activation," *J. Immunol.*, 166:936-944, American Association of Immunologists, US (2001).
Beeton, C. et al., "Targeting Effector Memory T Cells with a Selective Peptide Inhibitor of Kv1.3 Channels for Therapy of Autoimmune Diseases," *Mol. Pharmacol.*, 67:1369-1381, The American Society for Pharmacology and Experimental Therapeutics, US (2005).
Beeton, C. et al., "Kv1.3 channels are a therapeutic target for T cell-mediated autoimmune diseases," *Proc. Nat. Acad. Sci.*, 103:17414-17419, National Academy of Sciences, US (2006).
Brendel, J. and Peukert, S., "Blockers of the Kv1.5 channel for the treatment of atrial arrhythmias," *Expert Opin. Ther. Patents*, 12:1589-1598, Ashley Publications Ltd., USA (2002).
Cahalan, M. and Chandy, K., "Ion channels in the immune system as targets fro immunosuppression," *Current Opin. in Biotech.*, 8:749-756, Elsevier, UK (1997).
Chandy, K. et al., "$K^+$ channels as targets for specific immunomodulation," *Trends in Pharmacol. Sci.*, 25:280-289, Elsevier, UK (2004).
Colatsky, T. et al., "Channel Specificity in Antiarrhythmic Drug Action: Mechanism of Potassium Channel Block and Its Role in Suppressing and Aggravating Cardiac Arrhythmias," *Circulation*, 82:2235-2242, American Heart Association, US (1990).

(Continued)

*Primary Examiner* — Zinna Northington Davis
(74) *Attorney, Agent, or Firm* — Sterne, Kessler, Goldstein & Fox P.L.L.C.

(57) ABSTRACT

A compound of formula (I)

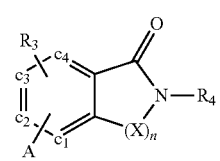

(I)

Or its salts or pharmaceutically acceptable derivatives thereof wherein;
A represents a chemical moiety with the general formula (II):

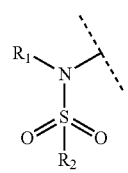

(II)

X is selected from a group consisting of $CH_2$, $C(=O)$, $CH(R_5)$, $C(R_5)(R_6)$ or $C(R_5)(R_6)CH_2$;

$R_1$ is selected from the group consisting of optionally substituted arylalkyl, and optionally substituted heteroarylalkyl;
$R_2$ is selected from the group consisting of optionally substituted aryl or optionally substituted heteroaryl or $NR_7R_8$;
$R_3$ $R_4$ $R_5$ $R_6$ $R_7$ and $R_8$ are as defined herein; and n=1 or 2 is provided.

Pharmaceutical compositions comprising the compounds are also provided. The compounds are useful in treating various conditions including arrhythmia.

25 Claims, No Drawings

OTHER PUBLICATIONS

Courtemanche, M. el al, "Ionic targets for drug therapy and atrial fibrillation-induced electrical remodeling: insights from a mathematical model," *Cardiovasc. Res.*, 42:477-489, Elsevier, UK (1999).

Fedida, D. et al., "Identity of a Novel Delayed Rectifier Current From Human Heart With a Cloned $K^{30}$ Channel Current," *Circ. Res.*, 73:210-216, American Heart Association, US (1993).

Felix, J. et al., "Identification and Biochemical Characterization of a Novel Nortriterpene Inhibitor of the Human Lymphocyte Voltage-Gated Potassium Channel, Kv1.3," *Biochem.*, 38:4922-4930, American Chemical Society, US (1999).

Feng, J. et al., "Antisense Oligodeoxynucleotides Directed Against Kv1.5 mRNA Specifically Inhibit Ultrarapid Delayed Rectifier $K^{30}$ Current in Cultured Adult Human Atrial Myocytes," *Circ. Res.*, 80:572-579, American Heart Association, US (1997).

Feng, J. et al., "Effects of Class III Antiarrhythmic Drugs on Transient Outward and Ultra-rapid Delayed Rectifier Currents in Human Atrial Myocytes," *J. Pharmacol. Exp. Ther.*, 281:384-392, The American Society for Pharmacology and Experimental Therapeutics, US (1997).

Ford, J. et al., "Potassium Channels: Gene Family, Therapeutic Relevance, High-Throughput Screening Technologies and Drug Discovery," *Prog. Drug. Res.*, 58:133-168, Birkhauser Verlag, CH (2002).

Garcia-Calvo, M. et al., "Purification, Characterization, and Biosynthesis of Margatoxin, a Component of *Centruroides maragr.* Venom That Selectively Inhibits Voltage-dependent Potassium Channel," *J. Biol. Chem.*, 268:18866-18874, The American Society for Biochemistry and Molecular Biology, US (1993).

Garcia, M. et al., "Purification and Characterization of Three Inhibitors of Voltage-Dependent $K^+$ Channels from *Leiurus quinquestriatus* var. *hebraeus* Venom," *Biochem*, 33:6834-6839, American Chemical Society, 'US (1994).

Godreau, D. et al., "Mechanisms of Action of Antiarrhythmic Agent Bertosamil on hKv1.5 Channels and Outward Potassium Current in Human Atrial Myocytes," *J. Pharmacol. Exp. Ther.* 300:612-620, The American Society for Pharmacology and Experimental Therapeutics, US (2002).

Gutman, G. et al., "International Union of Pharmacology. XLI. Compendium of Voltage-Gated Ion Channels: Potassium Channels, " *Pharmacol. Rev.* 55:583-586, The American Society for Pharmacology and Experimental Therapeutics, US (2003).

Hanson, D. et al., "UK-78,282, a novel piperidine compound that potently blocks the Kv1.3 voltage-gated potassium channel and inhibits human T cell activation," *Br. J. Pharmacol.*, 126:1707-1716, Stockton Press, UK (1999).

Herbert, S., "General Principles of the Structure of Ion Channels," *Am. J. Med.*, 104:87-98, Excerpta Medica, US (1998).

Kalman, K. et al., "ShK-Dap$^{22}$, a Potent Kv1.3-specific Immunosuppressive Polypeptide," *J. Biol. Chem.*, 273:32697-32707, The American Society for Biochemistry and Molecular Biology, USA (1998).

Knobloch, K. et al., 'Electrophysiological and antiarrhythmic effects of the novel $I_{Kur}$ channel blockers, S9947 and S20951, on left vs. right pig atrium in vivo in comparison with $I_{Kr}$ blockers dofetilide, azimilide, d,I-sotalol and ibutilide.

Koo, G. et al., "Correolide and Derivatives Are Novel Immunosuppressants Blocking the Lymphocyte Kv1.3 Potassium Channels," *Cell. Immunol.*, 197:99-107, Academic Press, UK (1999).

Koschak, A. et al., "Subunit Composition of Brain Voltage-gated Potassium Channels Determined by Hongotoxin-1, a Novel Peptide Derived from *Centruroides limbatus* Venom," *J. Biol. Chem.* 273:2639-2644, American Society for Biochemistry and Molecular Biology, US (1998).

Li, G. et al., "Evidence for Two Components of Delayed Rectifier $K^{30}$ Current in Human Ventricular Myocytes," *Circ. Res.* 78:689-696, The American Heart Association, US (1996).

Malayev, A. et al., "Mechanism of Clofiliium Block of the Human Kv1.5 Delayed Rectifier Potassium Channel," *Mol. Pharmacol.*, 47:198-205, The American Society for Pharmacology and Experimental Therapeutics, US (1995).

Marbán, E., "Cardic channelopathies," *Nature*, 415:213-218, MacMillan Magazines Ltd., UK (2002).

Matsuda, M., et al., "Inhibition by a novel anti-arrhythmic agent, NIP-142, of cloned human cardiac $K^{30}$ channel Kv1.5 current," *Life Sci.*, 68:2017-2024, Elsevier Science Inc., UK (2001).

Mouhat, S. et al., "$K^+$ channel types targeted by synthetic OSK1, a toxin from *Orthochirus scrobiculosus* scorpion venom," *Biochem. J.*, 385:95-104, Biochemical Society, UK (2005).

Nattel, S. et al., "Cardiac Ultrarapid Delayed Rectifiers: A Novel Potassium Current Family of Functional Similarity and Molecular Diversity," *Cell, Physiol. Biochem.*, 9:217-226, Karger, DE (1999).

Nattel, S., "Therapeutic implications of atrial fibrillation mechanisms: can mechanistic insights be used to improve AF management?," *Cardiovasc. Res.*, 54:347-360, Elsevier Science B.V., UK (2002).

Nguyen, A. et al., "Novel Nonpeptide Agents Potently Block the C-Type.Inactivated Conformation of Kv1.3 and Suppress T Cell Activation," *Mol. Pharmacol.*, 50:1672-1679, The American Society for Pharmacology and Experimental Therapeutics, US (1996).

Panyi, G. et al., "Ion channels and lymphocyte activation," *Immunol. Lett.*, 92:55-66, Elsevier B.V., UK (2004).

Pennington, M. et al., "Identification of Three Separate Binding Sites on SHK Toxin, a Potent Inhibitor of Voltage-Dependent Potassium Channels in Human T-Lymphocytes and Rat Brain," *Biochem. Biophys. Res. Commun.*, 219:696-701, Academic Press, Inc., UK (1996).

Péter M. et al. "Effect of Toxins Pi2 and Pi3 on Human T Lymphocyte Kv1.3 Channels: The Role of Glu7 and Lys24," *J. Membr. Biol.*, 179:13-25, Springer Verlag, US (2001).

Peukert, S. et al., "Identification, Synthesis, and Activity of Novel Blockers of the Voltage-Gated Potassium Channel Kv1.5," *J. Med. Chem.*, 46:486-498, American Chemical Society, US (2003).

Price, M. et al., "Charybdotoxin inibits proliferation and interleukin 2 production in human peripheral blood lymphocytes," *Proc. Natl. Acad. Sci.* 86:10171-10175, The National Academy of Sciences, US (1989).

Sands, S. et al., "Charybdotoxin Blocks Voltage-grated $K^{30}$ Channels in Human and Murine T Lymphocytes," *J. Gen. Physiol.* 93:10061-1074, Rockefeller University Press, US (1989).

Schmitz, A. et al., "Design of PAP-1, a Selective Small Molecule Kv1.3 Blocker, for the Suppression of Effector Memory T Cells in Autoimmune Diseases," *Mol. Pharmacol.*, 68:1254-1270, The American Society for Pharmacology and Experimental Therapeutics, US (2005).

Shieh, C. et al., "Potassium Channels: Molecular Defects, Diseases, and Therapeutic Opportunities," *Pharmacol. Rev.*, 52:557-594, The American Society for Pharmacology and Experimental Therapeutics, US (2000).

Triggle, D. et al., "Voltage-Gated Ion Channels as Drug Targets," WILEY-VHC Verlag GmbH & Co., KGaA, DE, pp. 214-274 (2005).

Vennekamp, J.et al., "Kv1.3-Blocking 5-Phenylalkoxypsoralens: A New Class of Immunomodulators," *Mol. Pharmacol.*, 65:1364-1374, The American Society for Pharmacology and Experimental Therapeutics, US (2004).

Wang, Z. et al., "Effects of Flecainide, Quinidine, and 4-Aminopyridine on Transient Outward and Ultrarapid Delayed Rectifier Currents in Human Atrial Myocytes," *J. Pharmacol. Exper. Therap.*, 272:184-196, The American Society for Pharmacology and Experimental Therapeutics, US (1995).

Wang, Z. et al., "Sustained Depolarization-Induced Outward Current in Human Atrial Myocytes: Evidence for a Novel Delayed Rectifier $K^+$ Current Similar to Kv1.5 Cloned Channel Currents," *Circ. Res.*, 73:1061-1076, American Heart Association, US (1993).

Wirth, K. et al., "Atrial effects of the novel $K^+$-channel-blocker AVE0118 in anesthetized pigs," *Cardiovasc. Res.*, 60:298-306, American Heart Association, US (2003).

Wulff, H. et al., "Alkoxypsoralens, Novel Nonpeptide Blockers of *Shaker*—Type $K^{30}$ Channels: Synthesis and Photoreactivity," *J. Med Chem.*, 41:4542-4549, American Chemical Society, US (1998).

Wulff, H. et al., "Potassium channels as therapeutic targets for autoimmune disorders," *Curr. Opin. Drug Dis.* 6:640-647, Current Drugs, US (2003).

Xie, M. et al., "Ion channel drug discovery expands into new disease areas," *Current Drug Discovery*, 31-33, Synta Pharmaceuticals, US (2004).

Internatinal Search Report for International Patent Application No. PCT/GB2010/001092, European Patent Office, Rijswijk, The Netherlands, mailed Sep. 1, 2010.

International Preliminary Report on Patentability for International Patent Application No. PCT/GB2010/001092, The International Bureau of WIPO, Geneva, Switzerland, mailed Dec. 6, 2011.

COMPOUNDS

FIELD OF THE INVENTION

The present invention relates to compounds of formula (I) which are potassium channel inhibitors. Compounds in this class may be useful as Kv1.3 inhibitors for immunomodulation and the treatment of autoimmune, chronic inflammatory, metabolic diseases and the like. Additionally, compounds in this class may also be useful as Kv1.5 inhibitors for the treatment or prevention of arrhythmias. Pharmaceutical compositions comprising the compounds and their use in the treatment of autoimmune and inflammatory diseases and in the treatment of arrhythmia are also provided.

BACKGROUND

Ion channels are proteins that span the lipid bilayer of the cell membrane and provide an aqueous pathway through which specific ions such as $Na^+$, $K^+$, $Ca^{2+}$ and $Cl^-$ can pass (Herbert, 1998). Potassium channels represent the largest and most diverse sub-group of ion channels and they play a central role in regulating the membrane potential and controlling cellular excitability (Armstrong & Hille, 1998). Potassium channels have been categorized into gene families based on their amino acid sequence and their biophysical properties (for nomenclature see Gutman et al., 2003).

Compounds which modulate potassium channels have multiple therapeutic applications in several disease areas including autoimmune, inflammatory, cardiovascular, neuronal, auditory, renal and metabolic mediated diseases (Shieh et al., 2000; Ford et al., 2002, Xie et al, 2004, Cahalan et al, 1997). The potassium channel Kv1.3 is found in a number of tissues including neurons, blood cells, osteoclasts, macrophages, epithelia, and T- and B-lymphocytes. Furthermore, Kv1.3 inhibition has been shown to modulate T-cell function which has implications in many autoimmune diseases including psoriasis, rheumatoid arthritis, multiple sclerosis, obesity, diabetes and inflammatory bowel disease (Beeton et al., 2006).

Kv1.3 Channel Blockers for Autoimmune Disorders

The role of autoreactive, late-stage, memory T-cells in the pathogenesis of a variety of autoimmune diseases including psoriasis, rheumatoid arthritis, multiple sclerosis, IBD and others is well established. Activation of $T_{EM}$ cells is followed by substantial up-regulation of Kv1.3 channel expression and, as a result, Kv1.3 becomes the predominant route of potassium efflux from the cell. Thus, selective blockade of Kv1.3 causes membrane depolarisation and inhibition of $Ca^{2+}$ influx, leading to inhibition of cytokine production and cell proliferation and function. Kv1.3 thus represents a novel therapeutic target of great interest for autoimmune disease control.

T-cells and Autoimmunity

T-cells are lymphocytes which play a central role in cell mediated immunity. One of the major forms of T-cell is the helper T-cell ($T_H$), also known as CD4+ cells which plays an essential role in the development of autoimmune diseases. Through the production of the cytokine interleukin 2 (IL-2), CD4+ T-cells can create the second main type of T-cell known as cytotoxic T-cells (CD8+). Naïve (inactive) CD4+ and CD8+ T-cells express both proteins (CCR7+CD45RA+) and use the chemokine receptor CCR7 as a key to gain entry into lymph nodes. Within lymph nodes, the naïve T-cells encounter antigen and through an activation process, change into "effector" T-cells that produce cytokines and proliferate. Once the ensuing immune response subsides, most naïve effectors die, but a few differentiate into long-lived central memory cells ($T_{CM}$). $T_{CM}$ cells, like naïve cells, use CCR7 to home to the lymph nodes to encounter their cognate antigen. Upon antigenic stimulation, $T_{CM}$ cells change into "$T_{CM}$ effector" cells that produce cytokines and proliferate. They too suffer the same fate as naïve effectors, the majority dying after the immune response wanes, leaving a few long-lived survivors for further challenge. Repeated antigenic challenge, as might happen in autoimmune diseases or in chronic infections, causes $T_{CM}$ cells to differentiate into short-lived "effector memory T-cells" ($T_{EM}$) that lack expression of both CCR7 and CD45RA, and do not need to home to lymph nodes for antigen-induced activation. A subset of CD8+ $T_{EM}$ cells reacquire CD45RA and become CCR7-CD45RA+ $T_{EMRA}$ cells. Upon activation, both CD4+ and CD8+ $T_{EM}$ cells change into $T_{EM}$ effectors that migrate rapidly to sites of inflammation and produce large amounts of the proinflammatory cytokines, interferon-γ (IFN-γ) and tumor necrosis factor α (TNFα). In addition, CD8+ $T_{EM}$ effectors carry large amounts of perforin and are therefore immensely destructive (Wulff et al, 2003, Beeton et al, 2005).

Functional Role of Kv1.3 in T-cells and Autoimmune Disorders

Human T-cells express two $K^+$ channels, Kv1.3 and IKCa1, that provide the counterbalance cation efflux necessary for the sustained elevation of cytosolic $Ca^{2+}$ levels required for gene transcription, proliferation and cytokine secretion (Panyi et al, 2004, Chandy et al, 2004). The Kv1.3 and IKCa1 (also known as KCa3.1) channels regulate membrane potential and facilitate $Ca^{2+}$ signaling in T-lymphocytes. Kv1.3 opens in response to membrane depolarisation and maintains the resting membrane potential (initiation phase), whereas IKCa1 opens in response to an increase in cytosolic $Ca^{2+}$ and hyperpolarises the membrane potential (Beeton et al, 2001). Selective blockade of $K^+$ channels leads to membrane depolarisation, which in turn inhibits $Ca^{2+}$ influx and shuts down cytokine production and cell proliferation. Early in vitro studies, using channel blocker toxins, clearly demonstrate that Kv1.3 channels are essential for the synthesis (gene activation) and secretion of the cytokine IL-2 after T-cell activation (Price et al, 1989) and provide a rationale for the potential therapeutic use of inhibitors of this channel in immunological disorders. The role of autoreactive T-cells in the pathogenesis of autoimmune diseases has clearly been demonstrated in animal models. Disease-specific, autoreactive T-cells in several other autoimmune diseases are also reported to exhibit a memory phenotype. Autoreactive $T_{EM}$ cells are also implicated in psoriasis, rheumatoid arthritis, multiple sclerosis, IBD, vitiligo, uveitis, pemphigus, inflammatory myopathies, Hashimito disease, and scleroderma (Beeton et al, 2005). "Late" memory T- and B-cells have been implicated in the disease progression and tissue damage in a number of autoimmune diseases, in transplant rejection and chronic graft-versus-host disease. Modulators of the Kv1.3 channel may allow selective targeting of disease-inducing effector memory T-cells and memory B-cells without compromising the normal immune response and as a result are likely to have a preferred side-affect profile than agents that bring about more general immunosuppression.

The observation that the Kv1.3 blocker margatoxin (MgTX) effectively suppressed the delayed-type hypersensitivity (DTH) response in vivo was provided by Koo et al, 1999. In addition MgTX was also shown to inhibit primary antibody response in non-sensitised animals (secondary antibody response was not affected by MgTX. These latter results are in agreement with the notion that Kv1.3 channels are predominant in resting T lymphocytes and regulate their function, while IKCa1 channels are more important in pre-activated T lymphocytes. Correolide (Koo et al, 1999) and PAP-1 (Schmitz et al, 2005) are novel immunosuppressants which block Kv1.3 channels and are effective in the DTH model. Because the cellular components involved in DTH response are similar to those found in autoimmune diseases and allograft rejection, the results obtained are very promising for the development of Kv1.3 channel blockers as new immunosuppressants.

In the early 1980's a number of compounds were reported to block Kv1.3 channels at micromolar to millimolar concentrations as described by Triggle et al, in "Voltage Gated Ion Channels as Drug Targets" these include classical Kv channel inhibitors such as 4-aminopyridine and tetramethylammonium, and other non specific compounds such as the calcium activated potassium channel blockers quinine and ceteidil, the phenothiazine antipscychotics chloropromazine and trifluoroperazine, the classical calcium channel inhibitors verapamil, diltiazem, nifedipine and nitrendipine, and the beta blocker propranolol.

Also in the 1980's natural products extracted from scorpions, snakes and other marine organisms were found to be potent inhibitors of Kv1.3 channels, these were primarily short peptides (<70 residues) that are stabilised by multiple sulphide bonds. The first of these potent inhibitors was isolated from the venom of the scorpion *Leiurus quinquestriatus hebraeus* and was named charybdotoxin (ChTX) (Sands et al, 1989), there after screening of other scorpion venoms led to the identification of more potent Kv1.3 blocking toxins, these include margatoxin (MgTX) (Garcia et al, 1993), agitoxin-2 (Garcia et al, 1994), hongotoxin (Koshchak et al, 1998), pandinus imperator toxin 2 (Pi2) (Peter et al, 2001) and orthochirus scrobiculosus (OSK1) (Mouhat et al, 2005) among others. With the exception of OSK1 (300 fold selective over the nearest related channel) none of the scorpion toxins were selective for Kv1.3.

One of the most potent and selective Kv1.3 blockers to date, which was extracted from sea anemone is stichodactyla helianthus toxin (Shk) (Pennington et al, 1996) this has been reported for the treatment of autoimmune disease through the blockade of Kv1.3 (U.S. Pat. No. 6,077,680). Shk and its synthetic derivative Shk-Dap[22] with improved selectivity profile display pico molar activity (Pennington et al, 1998) however, these peptides proved to have unfavourable properties for further development.

Recently more novel and selective small molecule Kv1.3 channel blockers have been reported for the management of autoimmune disorders. These include the iminodihydroquinolines WIN173173 and CP339818 (Nguyen et al., 1996), the benzhydryl piperidine UK-78,282 (Hanson et al. 1999), correolide (Felix et al., 1999), cyclohexyl-substituted benzamide PAC (U.S. Pat. No. 6,194,458, WO0025774), sulfamidebenzamidoindane (U.S. Pat. No. 6,083,986), Khellinone (Baell et al., 2004), dichloropenylpyrazolopyrimidine (WO-00140231) and psoralens (Wulff et al., 1998, Vennekamp et al., 2004, Schmitz et al., 2005).

Substituted arylsulfonamides have been reported widely to be useful ligands for intervention in a number of therapeurtic areas, these range from inhibitors of 11-beta-hydroxysteroid dehydrogenase type1, for the treatment and prevention of hyperglycemia in diseases such as type-2 diabetes (WO2004065351), inhibitors of mitotic kinesins as effective anti cancer agents (WO2007056078), inhibitors of Factor Xa useful in the treatment of arterial and venous thrombotic occlusive disorders, inflammation, cancer and neurodegenerative diseases (WO96/40100), inhibitors of BACE as an effective means for treating and preventing Alzheimer's and related diseases caused by the production of beta-amyloid (WO2005/030709). They have also been claimed as liver X receptor (LXR) modulators useful for the treatment or prevention of diseases associated with the activity of LXR's (WO2003082205) and for the treatment or prophylaxis of viral diseases, in particular for the treatment of Hepatitis C (WO 2007/110171).

Substituted bicyclic tertiary arylsulphonamides have been reported to be useful as inhibitors of glycogen associated protein phospharasel (PP1) for the prevention of metabolic disorders, particularly diabetes (WO2008113760); inhibitors of alpha2C adrenergic receptors for treating glaucoma, chronic pain, migraines, heart failure and psychotic disorders (WO2007024944); inhibitors of Kv1 voltage dependent potassium channels, through interruption of the interaction of the Kv channel with the Kv beta subunit, for treating a range of conditions from urinary tract disorders to pain, cardiac disorders to cell proliferative and metabolic disorders such as malignancy and diabetes (WO2008038053); and as antithrombotic agents with potential application in treating deep vein thrombosis and preventing occlusion in conditions such as stroke (U.S. Pat. No. 6,300,342).

It has now surprisingly been found that compounds of general formula (I) set out below act as inhibitors of potassium channels. These compounds are particularly useful for inhibiting the potassium channel Kv1.3 and treating diseases associated with the inhibition of the potassium channel Kv1.3. This invention is not limited to treating diseases mediated by Kv1.3, the compounds also being useful to treat diseases which require Kv1.5 potassium channel inhibition for example atrial fibrillation (Marban, 2002, Brendel and Peukert, 2002).

DESCRIPTION OF PRESENT INVENTION

Thus, in a first aspect, the present invention provides a compound of formula (I)

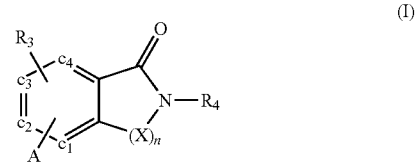

Or its salts or pharmaceutically acceptable derivatives thereof wherein;
A represents a chemical moiety with the general formula (II):

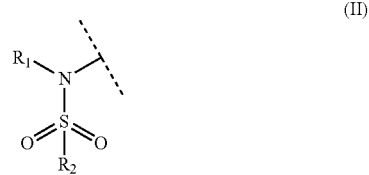

X is selected from a group consisting of $CH_2$, $C(=O)$, $CH(R_5)$, $C(R_5)(R_6)$ or $C(R_5)(R_6)CH_2$;
$R_1$ is selected from the group consisting of optionally substituted arylalkyl, and optionally substituted heteroarylalkyl;
$R_2$ is selected from the group consisting of optionally substituted aryl or optionally substituted heteroaryl or $NR_7R_8$;

$R_3$ is selected from the group consisting of hydrogen, halogen, hydroxyl, alkoxy, aryloxy, optionally substituted alkyl, optionally substituted amino, optionally substituted amino sulfonyl or nitrile;

$R_4$ is selected from the group consisting of hydrogen, optionally substituted alkyl, optionally substituted cycloalkyl, optionally substituted heterocycloalkyl, optionally substituted acyl, optionally substituted sulfonyl, optionally substituted sulfamoyl, optionally substituted aryl, optionally substituted arylalkyl, and optionally substituted heteroaryl;

$R_5$ and $R_6$ for each occurrence is optionally substituted alkyl;

$R_7$ and $R_8$ are the same or different and each represents hydrogen, optionally substituted alkyl, optionally substituted cycloalkyl, optionally substituted arylalkyl, optionally substituted aryl or optionally substituted heteroaryl;

n=1 or 2, with the proviso that when X is $C(R_5)(R_6)CH_2$, n is 1

As used herein, the following definitions shall apply unless otherwise indicated.

The term "optionally substituted" means that a group may be substituted by one or more substituents which may be the same or different. When otherwise not specified, these substituents are selected from alkyl, cycloalkyl, —O—C(halogen)$_3$ preferably —OCF$_3$, biaryl, carbocyclic aryl, heteroalicyclic, heteroaryl, acyl, amidino, amido, amino, alkyoxyamino, carbamoyl, carboxy, cyano, ether, hydroxyl, imino, halo, nitro, sulphamoyl, sulfonyl, sulphinyl, sulphenyl, sulfonamido or urea.

The term "alkyl group" as used herein, is typically a linear or branched alkyl group or moiety containing from 1 to 6 carbon atoms, preferably 2, 3, 4, or 5 carbon atoms such as a $C_{1-4}$ alkyl group or moiety, for example methyl, ethyl, n-propyl, i-propyl, butyl, i-butyl and t-butyl. An alkyl group or moiety may be unsubstituted or substituted at any position. Typically, it is unsubstituted or carries one two or three substituents. Suitable substituents include cyano, halogen, hydroxyl, alkylamino, dialkylamino, amido, alkylamido, dialkylamido, alkanoyl, alkoxy, sulfonamido, nitro, aryl and heteroaryl. The alkyl moiety may also be an "unsaturated alkyl" moiety, which means that it contains at least one alkene or alkyne moiety. An "alkene" moiety refers to a group consisting of at least two carbon atoms and at least one carbon-carbon double bond. An "alkyne" moiety refers to a group consisting of at least two carbon atoms and at least one carbon-carbon triple bond.

The term "cycloalkyl" as used herein refers to mono- or bicyclic ring or ring systems consisting of 3 to 11 carbon atoms i.e. 3, 4, 5, 6, 7, 8, 9, 10 or 11 carbon atoms. The ring system may be a "saturated ring", which means that the ring does not contain any alkene or alkyne moieties. The cycloalkyl group may also be an "unsaturated ring" which means that it contains at least one alkene or alkyne moiety and the ring system is not aromatic. The cycloalkyl group may be unsubstituted or substituted as defined herein. In addition to the above mentioned substituents one or more ring carbon atoms may also be bonded via a double bond to a group selected from NH, S and O. The cycloalkyl substituent may be bonded via a linker group such as a $C_{1-6}$ alkyl group, except where the optional substituent is alkyl. One or more hydrogens of the alkyl group in the linker may be replaced by a moiety selected from the group consisting of hydroxy, halo, cyano, amino, thiol, $C_{1-6}$alkoxy, $C_{1-6}$alkylthio, $C_{1-6}$alkylamino, and $C_{1-6}$dialkylamino.

The term "aryl group" as used herein, is typically a $C_{6-10}$ aryl group such as phenyl or naphthyl. A preferred aryl group is phenyl. An aryl group may be unsubstituted or substituted at any position. Typically, it carries 1, 2, 3 or 4 substituents. Suitable substituents include cyano, halogen, hydroxyl, nitro, trifluoromethyl, alkyl, alkylthio, alkoxy, amino, alkylamino, dialkylamino, alkanoyl, amido, N-alkylamido, NN-dialkylamino, sulfonamido, aryl and heteroaryl.

The term "carbocyclic" refers to a compound which contains one or more covalently closed ring structures and the atoms forming the backbone of the ring(s) are all carbon atoms. The term thus distinguishes carbocyclic from heterocyclic rings. Carbocyclic groups include both, a "cycloalkyl group", which means a non-aromatic carbocycle, and a "carbocyclic aryl" group, which means an aromatic carbocycle. The carbocyclic group may optionally be substituted as defined herein.

The term "heterocyclic" or "heterocyclo" as used herein refers to mono- or bicyclic rings or ring systems which include one or more heteroatoms selected from N, S and O. The rings or ring systems include 1 to 6 carbon atoms in addition to the heteroatom(s). The term heterocyclic group include both a "heteroalicyclic" group, which means a non-aromatic heterocycle and a "heteroaryl" group, which means an aromatic heterocycle. The heterocyclic moiety may be unsubstituted or substituted as defined herein and the substituents, when positioned adjacent to one another, may combine to form cycloalkyl or heteroalicyclic ring systems for example methylendioxy or difluoromethylendioxy. The heterocyclic substituent may be bonded via a carbon atom or a heteroatom. The heterocyclic group may also include the oxides of nitrogen and sulfur if nitrogen or sulfur are present in the ring.

The term "heteroaryl" as used herein refers to mono- or bicyclic ring or ring systems which include one or more heteroatoms selected from N, S and O. The rings or ring systems include 1 to 13 carbon atoms in addition to the heteroatom(s) and contain at least one aromatic ring with a heteroatom. The heteroaryl group may also include the oxides of nitrogen and sulfur if nitrogen or sulfur is present. Examples of monocyclic heteroaryl groups include, but are not limited to, furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl. Examples of bicyclic heterocycles include but are not limited to indolyl, benzofuranyl, benzothienyl, benzoxazolyl, benzothiazolyl, benzisoxazolyl, benzisothiazolyl, indazolyl, isoquinolinyl, quinolinyl, quinoxalinyl, cinnolinyl, phthalazinyl, quinazolinyl, benzotriazinyl and the like. Examples of tricyclic heterocycles include but are not limited to thianthrenyl, xanthenyl, phenoxathiinyl, carbazolyl, carbolinyl, phenanthridinyl, acridinyl, perimidinyl, phenanthrolinyl, phenazinyl, phenothiazinyl and phenoxazinyl. The heteroaryl group may be unsubstituted or substituted as defined herein. The substituents, when positioned adjacent to one another, may combine to form a cycloalkyl or heteroalicyclic ring for example methylendioxy and difluoromethylendioxy. The heteroaryl substituent may be bonded via a carbon atom or a heteroatom.

The term "arylalkyl", as used herein, refers to a chemical moiety of formula aryl-$C_{1-6}$alkyl or $C_{1-6}$alkyl-aryl as those terms are defined herein.

The term "heteroarylalkyl", used as herein, refers to a chemical moiety of formula heteroaryl-$C_{1-6}$alkyl or $C_{1-6}$alkyl-heteroaryl as those terms are defined herein.

The term "acyl", as used herein, refers to a chemical moiety of formula $(CH_2)yC(=O)Rz$ wherein y is 1-6

The term "amidino" refers to a chemical moiety with the formula $(CH_2)yC(=NH)NRzR'z$ wherein y is 1-6.

The term "amido" refers to both, a "C-amido" group which means a chemical moiety with the formula —C(=O)NRzR'z and a "N-amido" group which means a chemical moiety with the formula —NRzC(=O)R'z.

The term "amine" or "amino" refers to a chemical moiety of formula —NRzR'z. The definition of an amine is also understood to include their N-oxides.

A "cyano" group refers to a chemical moiety of formula —CN.

The term "hydroxy" or "hydroxyl" as used herein, refers to a chemical moiety of formula —OH.

The term "halogen" or "halo" refers to an atom selected from the group consisting of fluorine, chlorine, bromine and iodine.

The term "alkanoyl", as used herein, refers to a chemical moiety with the formula —C(=O)Rz.

The term "sulfone" or "sulfonyl" refers to a chemical moiety with the formula —S(=O)$_2$Rz.

The term "sulfinyl" refers to a chemical moiety with the formula —S(=O)Rz.

The term "sulfenyl" refers to a chemical moiety with the formula —SRz.

A "sulfamoyl" group refers to a chemical moiety with the formula —NRz-S(=O)$_2$NRzR'z.

The term "sulfonamido" refers to both an "S-sulfonamido" group which means a chemical moiety with the formula —S(=O)$_2$NRzR'z and an "N-sulfonamido" group which means a chemical moiety with the formula —N—S(=O)$_2$R'z.

The term "thiocarbonyl" refers to a chemical moiety with the formula (CH$_2$)yC(=S)Rz wherein y is 1-6.

The term "thio" or "thiol", as used herein, refers to a chemical moiety of formula —SH.

The term "thioamide" refers to both a "C-thioamido" group which means a chemical moiety with the formula (CH$_2$)yC(=S)NRzR'z and a "N-thioamido" group which means a chemical moiety with the formula (CH$_2$)yNRzC(=S)R'z wherein y is 1-6.

An "urea" group refers to a chemical moiety of formula —NRzC(=O)NRzR'z.

Rz and R'z are independently selected from the group consisting of hydrogen, $C_{1-6}$alkyl, cycloalkyl, $C_{1-6}$alkoxy, aryl-$C_{1-6}$alkyl, aryl and heteroaryl.

In a preferred embodiment:
X is CH$_2$, C(=O) or C(R$_5$)(R$_6$)CH$_2$.

The chemical moiety A is attached to the compound of formula (I) via chemical bond at C$_1$, C$_2$ or C$_3$.

Preferably R$_1$ is a chemical moiety of formula (III):

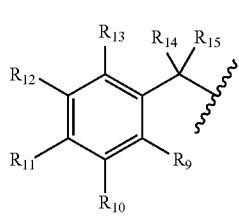

(III)

Wherein:
R$_9$, R$_{10}$, R$_{11}$, R$_{12}$ and R$_{13}$ are the same or different and each represents hydrogen, halogen, hydroxyl, optionally substituted amino, optionally substituted acyl, nitrile, optionally substituted $C_{1-3}$ alkyl or optionally substituted alkoxy;

R$_{14}$ and R$_{15}$ are the same or different and each represents hydrogen, hydroxyl, and optionally substituted $C_{1-3}$ alkyl. Preferably R$_{10}$, R$_{11}$ and R$_{12}$ are the same or different and each represents H, Cl, F, or CH$_3$.

R$_2$ is selected from compounds of formula (IV), (V) or (VI):

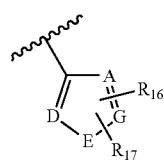

(IV)

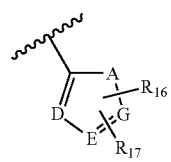

(V)

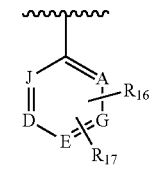

(VI)

Wherein:
A, D, E, G, and J are the same or different and each represents C, or N with the proviso that in each instance at least one of A, D, E, G, or J is N;
When R$_2$ is selected from compounds of formula (IV), E may also represent O or S; and
When R$_2$ is selected from compounds of formula (V), A may also represent O or S;
Preferred moities of formula (IV), (V) and (VI) are Imidazole, Pyrazole, Pyrrole, Oxazole, Oxadiazole, Thiazole, Thiadiazole, Pyridine, Pyrimidine, Pyrazine, Pyridazine, and Triazine. More preferably R$_2$ is selected from Imidazole, Pyrazole, or Pyridine.

R$_{16}$ and R$_{17}$ are the same or different and each represents hydrogen, halogen, hydroxyl, nitrile, optionally substituted amino, optionally substituted acyl, optionally substituted $C_{1-3}$ alkyl, optionally substituted arylalky, optionally substituted aryl or optionally substituted heteroaryl or may be taken together to form an optionally substituted saturated or partially saturated 5-7 membered heterocyclic or carbocyclic ring. Preferably R$_{16}$ and R$_{17}$ are alkyl, more preferably CH$_3$.

Alternatively, R$_2$ is selected from compounds of formula (VII)

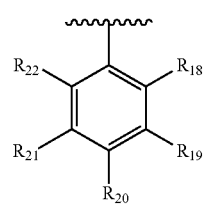

(VII)

R$_{18}$, R$_{19}$, R$_{20}$, R$_{21}$, and R$_{22}$ are the same or different and each represents hydrogen, halogen, hydroxyl, optionally substituted amino, optionally substituted acyl, nitrile, optionally substituted $C_{1-3}$ alkyl, any of the pairs R$_{18}$ and R$_{19}$, or R$_{19}$ and $R_{20}$, or $R_{20}$ and $R_{21}$, or $R_{21}$ and $R_{22}$ or may be taken together to form an optionally substituted saturated or partially saturated 5-7 membered heterocyclic or carbocyclic ring.

Preferred moities of formula (VII) include phenyl, fluorophenyl, chlorophenyl, cyanophenyl, aminophenyl, acetamidophenyl, tetrahydrobenzofuran, benzopyran, dihydrobenzodioxin, benzoxazinone, benzooxadiazole, benzodioxole, indoline, indole, indazole, and benzomorpholine. Preferably (VII) is selected from phenyl, fluorophenyl, cyanophenyl, tetrahydrobenzofuran, benzopyran, dihydrobenzodioxin, benzoxazinone, benzooxadiazole, benzodioxole, indoline, and benzomorpholine.

Preferably $R_3$ is H, F or $CH_3$. More preferably $R_3$ is H.

$R_4$ is preferably selected from the group consisting of hydrogen, optionally substituted alkyl, optionally substituted cycloalkyl, optionally substituted heterocycloalkyl, optionally substituted acyl, optionally substituted arylalkyl, and optionally substituted heteroaryl. Preferred examples include hydrogen, methyl, ethyl, propyl, isopropyl and 2-hydroxyethyl.

$R_5$ and $R_6$ are optionally substituted alkyl. More preferably, $R_5$ and $R_6$ are $CH_3$.

More preferred compounds are those where A is represented by formula (VIII);

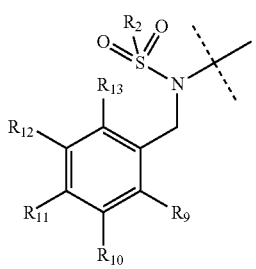

(VIII)

Wherein:

$R_2$ is selected from compounds of formula (III), (IV) (V) or (VI), and $R_9$, $R_{10}$, $R_{11}$, $R_{12}$ and $R_{13}$ are defined as above.

Most preferred compounds are those selected from compounds of formula (I) where the core structure is represented by (IX), (X), (XI);

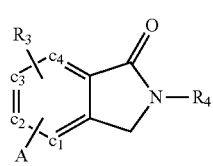

(IX)

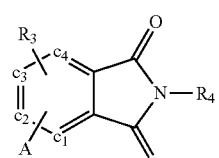

(X)

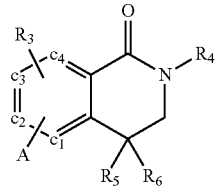

(XI)

Wherein;

A is a chemical moiety of formula (VIII), and $R_3$ and $R_4$ are as defined above.

Particularly preferred compounds of the invention include:
1-Methyl-1H-pyrazole-3-sulfonic acid (4-chloro-benzyl)-(2-ethyl-1-oxo-1,2,3,4-tetrahydro-isoquinolin-7-yl)-amide
Pyridine-3-sulfonic acid (40chloro-benzyl)-(2-ethyl-3-oxo-2,3-dihydro-1H-isoindol-5-yl)-amide
N-(4-Chloro-benzyl)-3-cyano-N-(1-oxo-1,2,3,4-tetrahydro-isoquinolin-7-yl)-benzenesulfonamide
Pyridine-3-sulfonic acid (4-chloro-benzyl)-[2-(2-hydroxy-ethyl)-1-oxo-1,2,3,4-tetrahydro-isoquinolin-7-yl]-amide
1-Methyl-1H-imidazole-4-sulfonic acid (4-chloro-benzyl)-(2-ethyl-4,4-dimethyl-1-oxo-1,2,3,4-tetrahydro-isoquinolin-7-yl)-amide
1-Methyl-1H-pyrazole-3-sulfonic acid (4-chloro-benzyl)-(1-oxo-1,2,3,4-tetrahydro-isoquinolin-7-yl)-amide
N-(4-Chloro-benzyl)-3-cyano-N-(1-oxo-1,2,3,4-tetrahydro-isoquinolin-7-yl)-benzenesulfonamide
1-Methyl-1H-pyrazole-3-sulfonic acid (4-chloro-benzyl)-(2-methyl-1-oxo-1,2,3,4-tetrahydro-isoquinolin-7-yl)-amide
1-Methyl-1H-pyrazole-3-sulfonic acid (4-chloro-benzyl)-[2-(2-hydroxy-ethyl)-1-oxo-1,2,3,4-tetrahydro-isoquinolin-7-yl]-amide
N-(4-Chloro-benzyl)-3-cyano-n-(2-ethyl-3-oxo-2,3-dihydro-1H-isoindol-5-yl)-benzene sulfonamide
N-(4-Chloro-benzyl)-3-cyano-N-(2-ethyl-1-oxo-2,3-dihydro-1H-isoindol-5-yl) benzene sulfonamide
Pyridine-3-sulfonic acid (4-chloro-benzyl)-(1-oxo-1,2,3,4-tetrahydro-isoquinolin-7-yl)-amide
1-Methyl-1H-imidazole-4-sulfonic acid (4-chloro-benzyl)-(2-ethyl-3-oxo-2,3-dihydro-1H-isoindol-5-yl)-amide
Pyridine-3-sulfonic acid 94-chloro-benzyl)-(4,4-dimethyl-1-oxo-1,2,3,4-tetrahydro-isoquinolin-7-yl)-amide
1-Methyl-1H-pyrazole-3-sulfonic acid (4-chloro-benzyl)-(4,4-dimethyl-1-oxo-1,2,3,4-tetrahydro-isoquinolin-7-yl)-amide
1-Methyl-1H-imidazole-4-sulfonic acid (4-chloro-benzyl)-(2-isopropyl-1,3-dioxo-2,3-dihydro-1H-isoindol-5-yl)-amide
1-Methyl-1H-pyrazole-3-sulfonic acid (4-chloro-benzyl)-(2-ethyl-1-oxo-2,3-dihydro-1H-isoindol-5-yl)-amide
1-Methyl-1H-pyrazole-3-sulfonic acid benzyl (2-ethyl-1-oxo-1,2,3,4-tetrahydro-isoquinolin-6-yl)-amide
1-Methyl-1H-imidazole-4-sulfonic acid (4-chloro-benzyl)-(4,4-dimethyl-1-oxo-1,2,3,4-tetrahydro-isoquinolin-7-yl)-amide
1-Methyl-1H-imidazole-4-sulfonic acid (4-chloro-benzyl)-(2-ethyl-1-oxo-2,3-dihydro-1H-isoindol-4-yl)-amide
1-Methyl-1H-imidazole-4-sulfonic acid (4-chloro-benzyl)-(2-ethyl-1-oxo-2,3-dihydro-1H-isoindol-5-yl)-amide
1-Methyl-1H-imidazole-4-sulfonic acid benzyl-(2-ethyl-1-oxo-1,2,3,4-tetrahydro-isoquinolin-6-yl)-amide.

As used herein, a pharmaceutically acceptable salt is a salt with a pharmaceutically acceptable acid or base. Pharmaceutically acceptable acids include both inorganic acids such as hydrochloric, sulphuric, phosphoric, diphosphoric, hydrobromic or nitric acid and organic acids such as citric, fumaric, maleic, malic, ascorbic, succinic, tartaric, benzoic, acetic, methanesulfonic, ethanesulfonic, benzenesulfonic or p-toluenesulfonic. Pharmaceutically acceptable bases include alkali metal (e.g. sodium or potassium) and alkali earth metal (e.g. calcium or magnesium) hydroxides and organic bases such as alkyl amines, arylalkyl amines or heterocyclic amines.

The compounds of the invention may contain one or more chiral centres. For the avoidance of doubt, the chemical structures depicted herein are intended to embrace all stereo isomers of the compounds shown, including racemic and non racemic mixtures and pure enantiomers and/or diastereoisomers.

As discussed herein, the compounds of the invention are useful in the treatment of various conditions. Thus, in a second aspect, the present invention provides a compound of formula (I) as defined herein for use in medicine. Preferably the compound is used to prevent or treat conditions which require inhibition of potassium channels, such as immunological disorders, including psoriasis, rheumatoid arthritis and multiple sclerosis.

In a further aspect the present invention provides a pharmaceutical formulation comprising at least one compound of formula (I) or as defined herein and optionally one or more excipients, carriers or diluents.

The compositions of the invention may be presented in unit dose forms containing a predetermined amount of each active ingredient per dose. Such a unit may be adapted to provide 5-100 mg/day of the compound, preferably either 5-15 mg/day, 10-30 mg/day, 25-50 mg/day 40-80 mg/day or 60-100 mg/day. For compounds of formula I, doses in the range 100-1000 mg/day are provided, preferably either 100-400 mg/day, 300-600 mg/day or 500-1000 mg/day. Such doses can be provided in a single dose or as a number of discrete doses. The ultimate dose will depend on the condition being treated, the route of administration and the age, weight and condition of the patient and will be at the doctor's discretion.

The compositions of the invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols or oils.

For applications to the eye or other external tissues, for example the mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administration to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or enemas.

Pharmaceutical formulations adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Preferred unit dosage formulations are those containing a daily dose or sub-dose, as herein above recited, or an appropriate fraction thereof, of an active ingredient.

It should be understood that in addition to the ingredients particularly mentioned above, the formulations may also include other agents conventional in the art having regard to the type of formulation in question, for example those suitable for oral administration may include flavouring agents.

The compositions of the invention can be used to treat conditions which require inhibition of potassium channels, for example in the treatment of immunological disorders and arrythmia. Thus, in further aspects, the present invention provides:

(i) A method of treating or preventing a disorder which requires potassium channel inhibition, eg immunological disorders comprising administering to a subject an effective amount of at least one compound of the invention or a pharmaceutical composition of the invention and (ii) the use of a compound of the invention in the manufacture of a medicament for use in potassium channel inhibition.

In particular, the medicament is for use in the treatment or prevention of psoriasis, rheumatoid arthritis, multiple sclerosis other immunological disorders and arrhythmia.

Methods

The compounds of formula (I) may be prepared by conventional routes, for example those set out in Schemes 1-4 shown below.

from ambient to reflux temperature. It is obvious and understood by those skilled in the art that compounds of formula (I) where $R_4$ is H may be converted to compounds of formula (I) where $R_4$ is alkyl or optionally substituted alky by reacting with a compound with the formula $R_4$—Y where $R_4$ is defined as alkyl or optionally substituted alkyl and Y is Cl or Br. Typically, this reaction is carried out in the presence of a

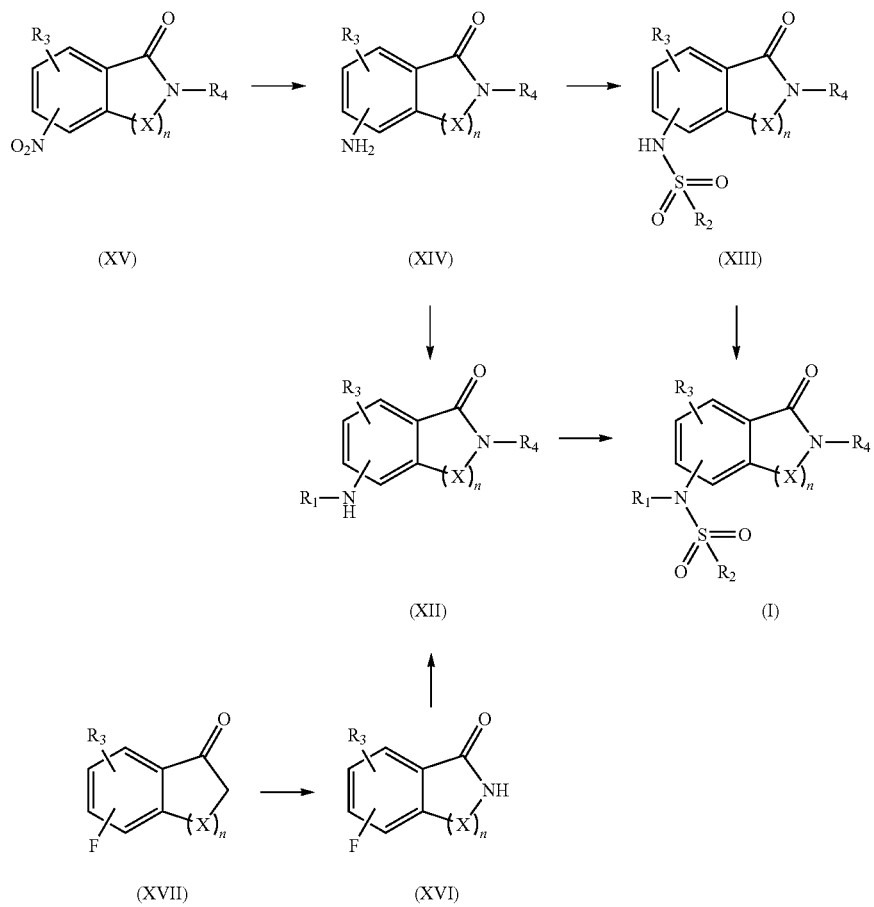

Compounds of formula (I) in which $R_4$ is H, alkyl or optionally substituted alkyl, and X is C=O or $CH_2$ or $C(R_5)(R_6)CH_2$, and $R_1$ $R_2$, $R_3$, and n are defined as above, may be prepared as in Scheme 1 from sulphonamides of the formula (XIII) in which X, $R_2$, $R_3$, $R_4$ and n are defined as above utilizing standard methods familiar to those skilled in the art such as, reaction with an electrophile of the formula $R_1$—Y where $R_1$ is defined as above and Y is Cl or Br in the presence of a base, for example cesium carbonate and a solvent such as tetrahydrofuran, acetonitrile or dichloromethane at a range of temperatures from ambient to reflux temperature. Alternatively, compounds of formula (I) in which X, $R_1$ $R_2$, $R_3$, $R_4$ and n are defined as above may be prepared from amines of the formula (XII) in which X, $R_1$, $R_3$, $R_4$ and n are defined as above by standard methods familiar to those skilled in the art such as, reaction with a sulfonyl or sulfamoyl chloride with the formula $R_2SO_2Cl$ in which $R_2$ is defined as above, in the presence of a base, for example pyridine, triethylamine or potassium carbonate and a solvent such as tetrahydrofuran, acetonitrile or dichloromethane, at a range of temperatures strong base, for example sodium hydride, a solvent such as tetrahydrofuran or dimethylformamide at a range of temperatures from ambient to reflux temperatures using microwave or conventional heating.

Compounds of formula (XIII) in which X, $R_2$, $R_3$, $R_4$ and n are defined as above, may be prepared from compounds of formula (XIV) in which X, $R_3$, $R_4$ and n are defined as above by standard methods familiar to those skilled in the art, such as reaction with a sulfamoyl or sulfamoyl chlorides with the formula $R_2SO_2Cl$ in which $R_2$ is defined as above, in the presence of a base, for example potassium carbonate, triethylamine or pyridine, and a solvent such as dichloromethane, tetrahydrofuran and acetonitrile, at a range of temperatures from ambient to reflux temperature.

Compounds of formula (XII) in which X, $R_1$, $R_3$, $R_4$ and n are defined as above, may be prepared from compounds of formula (XIV) in which X, $R_3$, $R_4$ and n are defined as above, by standard methods familiar to those skilled in the art such as, alkylation with an electrophile with the formula $R_1$—Y where $R_1$ is defined as above and Y is Cl or Br in the presence of a base, for example potassium carbonate, triethylamine or pyridine and a solvent such as dichloromethane, tetrahydrofuran and acetonitrile at a range of temperatures from ambient to reflux temperature. Alternatively, compounds of formula (XII) in which X, $R_1$, $R_3$, $R_4$ and n are defined as above, may be prepared from compounds of formula (XIV) in which X, $R_3$, $R_4$ and n are defined as above, by standard methods familiar to those skilled in the art, such as reductive amination with an aldehyde of the formula $R_1C\!\!=\!\!O$ where $R_1$ is defined as above in the presence of a reducing agent, for example sodium triacetoxyborohydride, and a solvent such as dichloromethane, tetrahydrofuran and acetonitrile at ambient temperature. Alternatively, compounds of formula (XII) in which $R_4$ is H and X, $R_1$, $R_3$ and n are defined as above, may be prepared from compounds of formula (XVI) in which X, $R_3$ and n are defined as above, by standard methods familiar to those skilled in the art, such as nucleophilic substitution (SnAr) of a fluorinated aryl system, bearing an electron sink such as the amide, with a primary amine with formula $R_1NH_2$ in which $R_1$ is defined as above, in the presence of a base, for example potassium carbonate at high temperatures using microwave or conventional heating.

Compounds of formula (XVI) in which is X is $CH_2$, n is 2 and $R_3$ is defined as above may be prepared from compounds of formula (XVII) in which X is $CH_2$, n is 1 and $R_3$ is defined as above using the Schmidt reaction conditions, typically the indanone (XVII) is reacted with reacted with methanesulphonic acid and sodium azide in a solvent such as dichloromethane at or below room temperature. Fluoro substituted indanones (XVII) are known and commercially available.

Compounds of formula (XIV) in which X, $R_3$, $R_4$ and n are defined as above, may be prepared from compounds of formula (XV) in which X, $R_3$, $R_4$ and n are defined as above, by standard methods familiar to those skilled in the art such as such as reduction using a reducing agent, for example Palladium/carbon (10% wt) and ammonium formate or tin(II) chloride in a suitable solvent such as dimethylformamide or ethanol, at ambient of temperatures.

Compounds of the formula (XV) in which X, $R_3$, $R_4$ and n are defined as above may be prepared by conventional routes described in Schemes 2-4 below

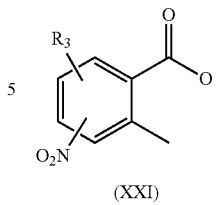

(XXI)

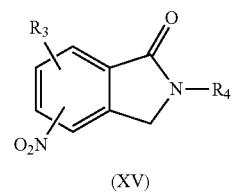

(XV)

Compounds of formula (XV) in which $R_3$, $R_4$ are defined as above may be prepared as in Scheme 2 from compounds of the formula (XVIII) in which Y is Br, Cl or any suitable leaving group and $R_3$ is defined as above, utilizing standard methods familiar to those skilled in the art for example reacting with a primary amine of the formula $R_4NH_2$ in which $R_4$ is defined as above in a solvent such as tetrahydrofuran at ambient temperatures.

Compounds of formula (XVIII) in which $R_3$ and Y are defined as above may be prepared from compounds of the formula (XIX) in which $R_3$ is defined as above by utilizing standard methods familiar to those skilled in the art, for example halogenation with a halo-succinamide of the formula (XX) where Y is Br or Cl, in the presence of a radical initiator for example ABCN or AIBN in a solvent such as carbon tetrachloride at ambient temperatures.

Compounds of formula (XIX) in which $R_3$ is defined as above may be prepared from compounds of formula (XXI) in which $R_3$ is defined as above by a standard method familiar to those skilled in the art, for example esterification with methanol in the presence of catalytic quantities of sulphuric acid at refluxing temperatures.

Compounds of formula (XXI) in which $R_3$ is defined as above are known compounds which are commercially available or may be prepared by standard methods familiar to those skilled in the art.

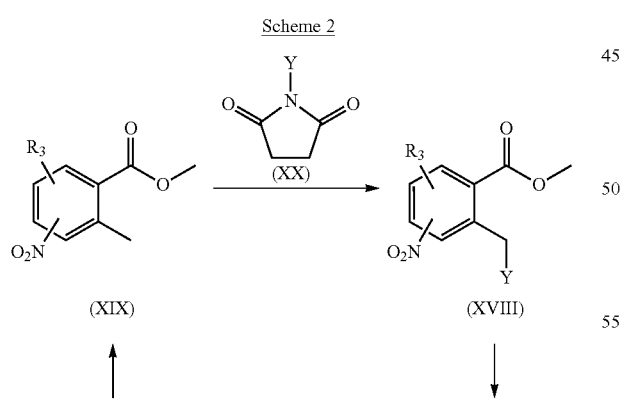

Scheme 2

Scheme 3

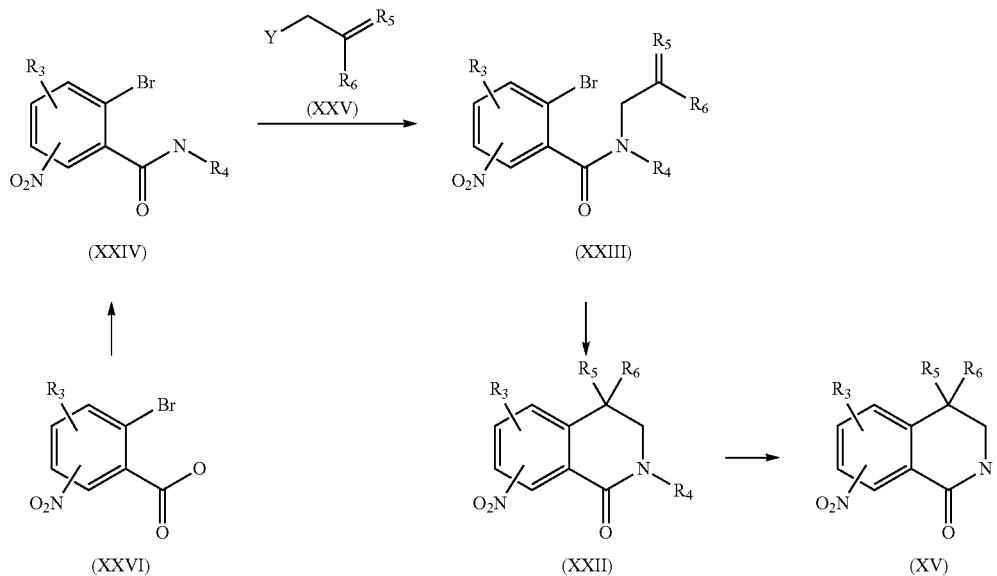

Compounds of formula (XV) in which $R_3$, $R_5$ and $R_6$ are defined as above may be prepared as in Scheme 3 from compounds of formula (XXII) in which $R_4$ is a protecting group for example para-methoxy benzyl (PMB) and $R_3$, $R_5$, and $R_6$ are defined as above, by standard method familiar to those skilled in the art using a deprotecting agent for example cerium ammonium nitrate in acetonitrile and water at a range of temperatures from 0° C. to ambient.

Compounds of formula (XXII) in which $R_4$ is a protecting group, for example PMB or defined as above and $R_3$, $R_5$ and $R_6$ are defined as above may be prepared from compounds of formula (XXIII) in which $R_3$, $R_4$, $R_5$ and $R_6$ are defined as above by standard method familiar to those skilled in the art such as intra-molecular palladium catalysed coupling, for example using palladium (II) acetate in the presence of tetraethylammonium chloride, sodium formate and sodium actete in a suitable solvent such as dimethyl formamdide at elevated temperatures.

Compounds of formula (XXIII) in which $R_3$, $R_4$, $R_5$ and $R_6$ are defined as above may be prepared from compounds of formula (XXIV) in which $R_3$ and $R_4$ are defined as above, by a standard method familiar to those skilled in the art, for example reacting with an electrophile of the formula (XXV) in which $R_5$ and $R_6$ are defined as above and Y is Cl or Br in the presence of a base, such as sodium hydride in a solvent such as dimethylformamide at a range of temperatures from −78 to 0° C.

Compounds of formula (XXIV) in which $R_3$ and $R_4$ are defined as above may be prepared from compounds of formula (XXVI) in which $R_3$ is defined as above, and a primary amine of the formula $R_4NH_2$ in which $R_4$ is paramethoxy benzyl or defined as above. Typically, this reaction is carried out using a coupling reagent such as 1-ethyl-3-(3-dimethylaminopropyl)-carbodiimide (EDC) or 2-(7-aza-1H-benztriazole-1-yl)-1,1,3,3-tetramethyluronium hexafluorophosphate (HATU) utilising standard methods familiar to those skilled in the art such as reaction in solvent such as tetrahydrofuran, acetonitrile or dimethylformamide at a range of temperatures from ambient to reflux temperature.

Compounds of formula (XXVI) are known compounds which are commercially available or may be prepared by standard methods familiar to those skilled in the art.

Scheme 4

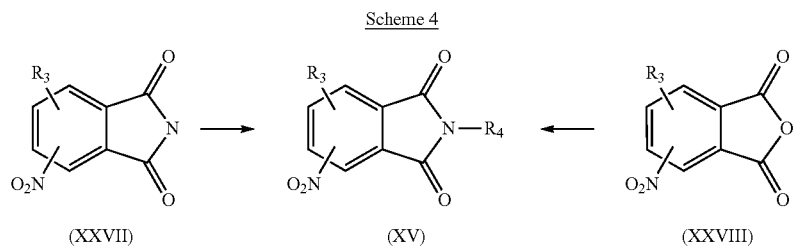

Compounds of formula (XV) in which $R_3$ and $R_4$ are defined as above may be prepared as in Scheme 4 from compounds of formula (XXVII) in which $R_3$ is defined as above and an alcohol of the formula $R_4$—OH, where $R_4$ is defined as above, utilizing the Mitsunobu reaction conditions, typically the reaction is carried out in the presence triphenylphosphine and an azodicarboxylate such diethylazodicarboxylate (DEAD) or diisopropylazodicarboxylate (DIAD) in a solvent such as THF at room ambient temperature. Alternatively compounds of formula (XV) in which $R_3$ and $R_4$ are defined as above may also be prepared from compounds of formula (XXVIII) in which $R_3$ is defined as above and primary amines of the formula $R_4$—$NH_2$ in which $R_4$ is defined as above.

Compounds of formula (XXVII) and (XXVIII) are known compounds which are commercially available or may be prepared by standard methods familiar to those skilled in the art.

EXPERIMENTAL

Examples

The HPLC analysis was conducted using one or more of the following methods:

Solvent: [MeCN-0.05% $HCO_2H$:$H_2O$-0.1% $HCO_2H$], 10-95% gradient 3 min, 95% 2.5 min; Column: Phenomenex Gemini 50×4.6 mm i.d., C18 reverse phase; Flow rate: 0.75 mL/min unless otherwise indicated.

Solvent: [MeCN—$H_2O$/0.01% $HCO_2H$], 5-95% gradient 5 min, 95% 3 min; Column: Phenomenex Gemini 50×4.6 mm i.d., C18 reverse phase; Flow rate: 1.5 mL/min unless otherwise indicated.

Solvent: [MeCN—$H_2O$/0.1% $HCO_2H$], 5-95% gradient 3.5 min, 95% 2 min; Column: Phenomenex Gemini 50×3 mm i.d., C18 reverse phase; Flow rate: 1 mL/min unless otherwise indicated.

Solvent: [MeCN—$H_2O$/0.1% $HCO_2H$], 5-95% gradient 6 min, 95% 3 min; Column: Phenomenex Gemini 50×4.6 mm i.d., C18 reverse phase; Flow rate: 1 mL/min unless otherwise indicated.

The preparative HPLC purification was conducted in the following manner:

Solvent: [MeCN-0.05% $HCO_2H$:$H_2O$-0.1% $HCO_2H$], 5-95% gradient 12 min, 95% 3 min; Waters X-Bridge 100×19 mm i.d., C18 reverse phase; Flow rate: 16 mL/min unless otherwise indicated.

Example 1

1-Methyl-1H-imidazole-4-sulfonic acid (4-chloro-benzyl)-(2-ethyl-1-oxo-2,3-dihydro-1H-isoindol-5-yl)-amide (Method A)

i) 2-Methyl-4-nitro-benzoic acid methyl ester

2-Methyl-4-nitrobenzoic acid (2.00 g, 11.00 mmol) was stirred in concentrated sulfuric acid (0.6 ml) and methanol (25 ml) at reflux for 15 hrs. Reaction was cooled and the solvent evaporated. The resulting residue was partitioned between water and dichloromethane and the organic phase separated. The aqueous phase was extracted with dichloromethane (×3) and the combined organics washed with brine, then dried ($MgSO_4$) and evaporated in vacuo to yield the title compound as a pale yellow solid (1.89 g, 96%). HPLC retention time 4.39 min.

The following compound was synthesised according to the method described using appropriate starting materials;
2-Methyl-5-nitro-benzoic acid methyl ester ii) 2-Bromomethyl-4-nitro-benzoic acid methyl ester N-Bromosuccinimide (2.18 g, 12.30 mmol) was added to a stirred solution of 2-methyl-4-nitro-benzoic acid methyl ester (2 g, 10.25 mmol) and ABCN (626 mg, 2.56 mmol) in carbon tetra-chloride (80 ml) at room temperature. The reaction was heated at reflux for 2 hrs and then allowed to cool to room temperature and stirred for 15 hrs. The solvent was evaporated in vacuo and the resulting residue filtered through a pad of silica (eluting with dichloromethane). The solvent was evaporated in vacuo to afford the title compound as a yellow solid (2.70 g, 96%). HPLC retention time 4.49 min. Mass spectrum (ES+) m/z 256 (M+H).

The following compounds were synthesised according to the method described using appropriate starting materials or commercially available;
2-Bromomethyl-5-nitro-benzoic acid methyl ester
2-Bromomethyl-3-nitro-benzoic acid methyl ester.

iii) 2-Ethyl-5-nitro-2,3-dihydro-isoindol-1-one

2-Bromomethyl-4-nitro-benzoic acid methyl ester (1.0 g, 3.64 mmol) was stirred in ethylamine (30 ml, 2.0M solution in THF) at room temperature. The reaction was stirred for 3 hrs, after which time the solvent was evaporated in vacuo and the crude residue triturated with diethyl ether. The resulting orange solid was filtered and dried in a vacuum oven (40° C.) to afford the title compound (634 mg, 85%). HPLC retention time 3.56 min. Mass spectrum (ES+) m/z 207 (M+H).

The following compounds were synthesised according to the method described using appropriate starting materials;
2-Ethyl-6-nitro-2,3-dihydro-isoindol-1-one
2-Ethyl-4-nitro-2,3-dihydro-isoindol-1-one iv) 5-Amino-2-ethyl-2,3-dihydro-isoindol-1-one Palladium/Carbon (10% wt) (63 mg, 0.30 mmol) was added to a stirred solution of 2-ethyl-5-nitro-2,3-dihydro-isoindol-1-one (634 mg, 3.06 mmol) and ammonium formate (949 mg, 15.31 mmol) in anhydrous DMF (12 ml) at room temperature. The resulting suspension was heated at reflux for 1 hr, then cooled and filtered through a pad of celite. The solvent was evaporated in vacuo and the crude residue purified by flash column chromatography (5% methanol in dichloromethane) to yield the title compound as a pale yellow oil (530 mg, 98%). HPLC retention time 0.95 min. Mass spectrum (ES+) m/z 177 (M+H).

The following compounds were synthesised according to the method described using appropriate starting materials;
6-Amino-2-ethyl-2,3-dihydro-isoindol-1-one
4-Amino-2-ethyl-2,3-dihydro-isoindol-1-one v) 5-(4-Chloro-benzylamino)-2-ethyl-2,3-dihydro-isoindol-1-one Sodium triacetoxyborohydride (1.28 g, 6.10 mmol) was added to a stirred solution of 5-amino-2-ethyl-2,3-dihydro-isoindol-1-one (540 mg, 3.05 mmol), 4-chlorobenzaldehyde (854 mg, 6.10 mmol) and acetic acid (183 μl, 3.05 mmol) in anhydrous acetonitrile (12 ml) at room temperature. The reaction was stirred overnight and quenched with the addition of water. The organic phase was separated, washed with brine, then dried ($MgSO_4$) and evaporated in vacuo. The resulting residue was purified by flash column chromatography (0 to 20% ethyl acetate in dichloromethane) to yield the title compound as a light brown solid (148 mg, 16%). HPLC retention time 4.23 min. Mass spectrum (ES+) m/z 301 (M+H).

The following compound was synthesised according to the method described using appropriate starting materials;
6-(4-Chloro-benzylamino)-2-ethyl-2,3-dihydro-isoindol-1-one
4-(4-Chloro-benzylamino)-2-ethyl-2,3-dihydro-isoindol-1-one vi) 1-Methyl-1H-imidazole-4-sulfonic acid (4-chloro-benzyl)-(2-ethyl-1-oxo-2,3-dihydro-1H-isoindol-5-yl)-amide To a stirred solution of 5-(4-Chloro-benzylamino)-2-ethyl-2,3-dihydro-isoindol-1-one (40 mg, 0.133 mmol) and pyridine (23 μM, 0.29 mmol) in dry acetonitrile (1 ml) was added 1-methyl-1H-imidazole-4-sulfonyl chloride (52 mg, 0.29 mmol) and the reaction heated to 150° C. in a microwave for 0.5 hrs. The reaction was filtered and purified by preparative HPLC (Method B) to afford the title compound as an off white solid (17 mg, 25%). HPLC retention time 4.00 min. Mass spectrum (ES+) m/z 445 (M+H).

Other compounds prepared by Method A as described for example 1 using the appropriate starting materials are listed in TABLE 1.

Example 2

1-Methyl-1H-pyrazole-3-sulfonic acid (4-chloro-benzyl)-(2-ethyl-1-oxo-1,2,3,4-tetrahydro-isoquinolin-7-yl)-amide (METHOD B)

i) 7-Benzylamino-3,4-dihydro-2H-isoquinolin-1-one

Sodium triacetoxyborohydride (1.29 g, 6.16 mmol) was added to a stirred solution of 7-amino-3,4-dihydro-2H-isoquinolin-1-one (500 mg, 3.08 mmol), 4-chlorobenzaldehyde (431 mg, 3.08 mmol) and acetic acid (183 μl, 3.08 mmol) in anhydrous dichloromethane (25 ml) at room temperature. The reaction was stirred overnight and quenched with the addition of water. The organic phase was separated, washed with brine, then dried (MgSO$_4$) and evaporated in vacuo. The resulting residue was purified by flash column chromatography (50% ethyl acetate in dichloromethane) to yield the title compound as a pale yellow solid (287 mg, 16%). HPLC retention time 4.09 min. Mass spectrum (ES+) m/z 287 (M+H).

ii) 1-Methyl-1H-pyrazole-3-sulfonic acid (4-chloro-benzyl)-(1-oxo-1,2,3,4-tetrahydro-isoquinolin-7-yl)-amide To a stirred solution of 7-benzylamino-3,4-dihydro-2H-isoquinolin-1-one (100 mg, 0.34 mmol) and pyridine (63 μl, 0.77 mmol) in anhydrous dichloromethane (2 ml) was added 1-methyl-1H-pyrazole-3-sulfonyl chloride (138 mg, 0.77 mmol) and the reaction heated at reflux for 15 hrs. The reaction was cooled and the solvent evaporated in vacuo. The crude residue was purified by flash column chromatography (50% ethyl acetate in dichloromethane) to afford the title compound as a colourless solid (63 mg, 41%). HPLC retention time 4.16 min. Mass spectrum (ES+) m/z 431 (M+H).

The following compound was synthesised according to the method described using appropriate starting materials;
N-(4-Chloro-benzyl)-3-cyano-N-(1-oxo-1,2,3,4-tetrahydro-isoquinolin-7-yl)-benzenesulfonamide
Pyridine-3-sulfonic acid (4-chloro-benzyl)-(1-oxo-1,2,3,4-tetrahydro-isoquinolin-7-yl)-amide iii) 1-Methyl-1H-pyrazole-3-sulfonic acid (4-chloro-benzyl)-(2-ethyl-1-oxo-1,2,3,4-tetrahydro-isoquinolin-7-yl)-amide To a suspension of 1-methyl-1H-pyrazole-3-sulfonic acid (4-chloro-benzyl)-(1-oxo-1,2,3,4-tetrahydro-isoquinolin-7-yl)-amide (20 mg, 0.046 mmol) and sodium hydride (3 mg, 0.055 mmol) in anhydrous THF (1 ml) was added iodoethane (8 μl, 0.055 mmol) and the reaction heated to 110° C. in a microwave for 0.5 h. The solvent was evaporated in vacuo and the resulting residue purified by preparative HPLC (Method B) to yield the title compound as a colourless solid (5 mg, 24%). HPLC retention time 4.34 min. Mass spectrum (ES+) m/z 459 (M+H).

Other compounds prepared by Method B as described for example 2 using the appropriate starting materials are listed in TABLE 1

Example 3

N-(4-Chloro-benzyl)-3-cyano-N-[2-(2-hydroxy-ethyl)-1-oxo-1,2,3,4-tetrahydro-isoquinolin-7-yl]-benzenesulfonamide (METHOD B)

N-(4-Chloro-benzyl)-3-cyano-N-(1-oxo-1,2,3,4-tetrahydro-isoquinolin-7-yl)-benzenesulfonamide (20 mg, 0.042 mmol) was stirred in dry DMF (5 ml) under nitrogen at 0° C. Sodium Hydride (8.8 mg, 0.022 mmol) was added and the mixture stirred for 5 minutes. 2-(2-bromoethoxytetrahydropyran) (33 μl, 0.022 mmol) was added and the reaction stirred for 30 minutes at 0° C. The DMF was removed in vacuo and the residue purified by prep HPLC. The residue was dissolved in Methanol (5 ml). To this solution was added 2M HCl (0.5 ml) and the mixture stirred at room temperature for 10 minutes until no starting material was observed on TLC (ethyl acetate). Solvents were removed and the residue purified by prep TLC (ethyl acetate) to give N-(4-Chloro-benzyl)-3-cyano-N-[2-(2-hydroxy-ethyl)-1-oxo-1,2,3,4-tetrahydro-isoquinolin-7-yl]-benzenesulfonamide as a colourless oil. Yield=11.7 mg. LCMS: ES+; 4.28 min; 496;

Other compounds prepared by Method B as described for example 2a using the appropriate starting materials are listed in TABLE 1.

Example 4

1-Methyl-1H-pyrazole-3-sulfonic acid benzyl (2-ethyl-1-oxo-1,2,3,4-tetrahydro-isoquinolin-6-yl)-amide (METHOD C)

i) 6-Fluoro-3,4-dihydro-2H-isoquinolin-1-one

To a solution of 5-fluoro-1-indanone (1.5 g, 10 mmol) and methanesulfonic acid (6 ml, 90 mmol) in anhydrous dichloromethane (6 ml) was added sodium azide (1.30 g, 20 mmol) whilst maintaining the temperature of the reaction between 21 and 26° C. The reaction was stirred for 15 hrs and then cooled in ice and basified using 5N sodium hydroxide solution. The organic phase was separated and the aqueous phase extracted with dichloromethane (2×10 ml). The combined organics were washed with water and brine, then dried (MgSO$_4$) and evaporated in vacuo. The resulting residue was purified by flash column chromatography (50% ethyl acetate in dichloromethane) to afford the title compound as a light brown solid (1.0 g, 61%). HPLC retention time 3.18 min. Mass spectrum (ES+) m/z 166 (M+H).

ii) 6-Benzylamino-3,4-dihydro-2H-isoquinolin-1-one

A solution of 6-fluoro-3,4-dihydro-2H-isoquinolin-1-one (300 mg, 1.81 mmol) and potassium carbonate (550 mg, 3.98 mmol) in benzylamine (1.5 ml) was stirred at 180° C. in a microwave for 2 hrs. The solvent was evaporated and the resulting residue partitioned between ethyl acetate (10 ml)

and water (10 ml). The organic phase was separated, washed with brine (10 ml), then dried (MgSO₄) and evaporated in vacuo. The crude residue was purified by preparative HPLC (Method A) to yield the title compound as a colourless solid (80 mg, 18%). HPLC retention time 3.81 min. Mass spectrum (ES+) m/z 253 (M+H).

iii) 1-Methyl-1H-pyrazole-3-sulfonic acid benzyl-(1-oxo-1,2,3,4-tetrahydro-isoquinolin-6-yl)-amide To a stirred solution of 6-benzylamino-3,4-dihydro-2H-isoquinolin-1-one (45 mg, 0.18 mmol) and pyridine (31 μl, 0.39 mmol) in anhydrous acetonitrile (1 ml) was added 1-methyl-1H-pyrazole-3-sulfonyl chloride (70 mg, 0.39 mmol) and the reaction heated to 150° C. in a microwave for 0.5 hrs. The solvent was evaporated in vacuo and the crude residue purified by preparative tlc (5% methanol in dichloromethane) to afford the title compound as a yellow solid (10 mg, 14%). HPLC retention time 3.83 min. Mass spectrum (ES+) m/z 397 (M+H).

vi) 1-Methyl-1H-pyrazole-3-sulfonic acid benzyl (2-ethyl-1-oxo-1,2,3,4-tetrahydro-isoquinolin-6-yl)-amide To a suspension of 1-methyl-1H-pyrazole-3-sulfonic acid benzyl-(1-oxo-1,2,3,4-tetrahydro-isoquinolin-6-yl)-amide (9 mg, 0.022 mmol) and sodium hydride (2 mg of a 60% dispersion in mineral oil, 0.045 mmol) in anhydrous THF (0.5 ml) was added iodoethane (2 μl, 0.045 mmol) and the reaction heated to 110° C. in a microwave for 0.5 hrs. The solvent was evaporated in vacuo and the resulting residue purified by preparative HPLC (Method B) to yield the title compound as a colourless solid (4 mg, 24%). HPLC retention time 4.14 min. Mass spectrum (ES+) m/z 425 (M+H).

Other compounds prepared by Method C as described for example 4 using the appropriate starting materials are listed in TABLE 1

Example 5

1-Methyl-1H-imidazole-4-sulfonic acid (4-chloro-benzyl)-(2-ethyl-4,4-dimethyl-1-oxo-1,2,3,4-tetrahydro-isoquinolin-7-yl)-amide (METHOD D)

i) 2-Bromo-N-ethyl-5-nitro-benzamide

To a stirred solution of HATU (501 mg, 1.32 mmol), 2-bromo-5-nitrobenzoic acid (325 mg, 1.32 mmol) and diisopropyl ethylamine (642 μl, 3.90 mmol) in anhydrous acetonitrile (20 ml) at room temperature was added ethylamine (725 μl of a 2.0M solution in THF, 1.45 mmol) and the reaction stirred for 15 hrs. The solvent was evaporated in vacuo and the crude residue purified by flash column chromatography (20% ethyl acetate in petroleum ether) to afford the title compound as a pale yellow solid (155 mg, 43%). HPLC retention time 3.72 min. Mass spectrum (ES+) m/z 273 (M+H).

The following compound was synthesised according to the method described using appropriate starting materials; 2-Bromo-N-(4-methoxy-benzyl)-5-nitro-benzamide ii) 2-Bromo-N-ethyl-N-(2-methyl-allyl)-5-nitro-benzamide

2-Bromo-N-ethyl-5-nitro-benzamide (150 mg, 0.55 mmol) in anhydrous DMF (2 ml) was added dropwise to a stirred suspension of sodium hydride (44 mg of 60% dispersion in mineral oil, 1.10 mmol) in anhydrous DMF (5 ml) at −78° C. The reaction was stirred for 0.25 hrs and then allowed to warm to 0° C. 3-Bromo-2-methylpropene (111 μl, 1.10 mmol) was then added and the reaction stirred for a further 1 hr at 0° C., after this time the solvent was evaporated in vacuo and the resulting residue partitioned between water and ethyl acetate. The organic phase was separated, washed with brine, then dried (MgSO₄) and evaporated in vacuo to afford the title compound as a colourless solid (150 mg, 84%). HPLC retention time 4.46 min. Mass spectrum (ES+) m/z 327 (M+H).

The following compound was synthesised according to the method described using appropriate starting materials; 2-Bromo-N-(4-methoxy-benzyl)-N-(2-methyl-allyl)-5-nitro-benzamide iii) 2-Ethyl-4,4-dimethyl-7-nitro-3,4-dihydro-2H-isoquinolin-1-one

To a stirred de-gassed solution of 2-bromo-N-ethyl-N-(2-methyl-allyl)-5-nitro-benzamide (150 mg, 0.46 mmol), tetraethylammonium chloride (84 mg, 0.46 mmol), sodium formate (34 mg, 0.50 mmol) and sodium acetate (82 mg, 1.01 mmol) in anhydrous DMF (10 ml) was added palladium(II) acetate (10 mg, 0.046 mmol) and the reaction stirred at 70° C. for 15 hrs. The reaction was cooled to room temperature and filtered through a pad of celite. The solvent was evaporated in vacuo and the resulting residue purified by flash column chromatography (20% ethyl acetate in dichloromethane) to afford the title compound as a yellow solid (110 mg, 96%). HPLC retention time 4.21 min. Mass spectrum (ES+) m/z 249 (M+H).

The following compound was synthesised according to the method described using appropriate starting materials; 2-(4-Methoxy-benzyl)-4,4-dimethyl-7-nitro-3,4-dihydro-2H-isoquinolin-1-one iv) 7-Amino-2-ethyl-4,4-dimethyl-3,4-dihydro-2H-isoquinolin-1-one

Palladium/Carbon (10% wt) (12 mg, 0.04 mmol) was added to a stirred solution of 2-ethyl-4,4-dimethyl-7-nitro-3,4-dihydro-2H-isoquinolin-1-one (110 mg, 0.44 mmol) and ammonium formate (137 mg, 2.21 mmol) in anhydrous DMF (6 ml) at room temperature. The resulting suspension was heated at reflux for 1hr, then cooled and filtered through a pad of celite. The solvent was evaporated in vacuo and the crude residue purified by flash column chromatography (60% ethyl acetate in dichloromethane) to afford the title compound as a pale yellow solid (40 mg, 98%). HPLC retention time 2.99 min. Mass spectrum (ES+) m/z 219 (M+H).

v) 7-(4-Chloro-benzylamino)-2-ethyl-4,4-dimethyl-3,4-dihydro-2H-isoquinolin-1-one Sodium triacetoxyborohydride (77 mg, 0.36 mmol) was added to a stirred solution of 7-amino-2-ethyl-4,4-dimethyl-3,4-dihydro-2H-isoquinolin-1-one (40 mg, 0.18 mmol), 4-chlorobenzaldehyde (31 mg, 0.22 mmol) and acetic acid (11 μl, 0.18 mmol) in anhydrous dichloromethane (6 ml) at room temperature. The reaction was stirred overnight and quenched with the addition of water. The organic phase was separated, washed with brine, then dried (MgSO₄) and evaporated in vacuo. The resulting residue was purified by preparative tlc (20% ethyl acetate in petroleum ether) to afford the title compound as a colourless solid (20 mg, 32%). HPLC retention time 4.78 min. Mass spectrum (ES+) m/z 343 (M+H).

vi) 1-Methyl-1H-imidazole-4-sulfonic acid (4-chloro-benzyl)-(2-ethyl-4,4-dimethyl-1-oxo-1,2,3,4-tetrahydro-isoquinolin-7-yl)-amide To a stirred solution of 7-(4-chloro-benzylamino)-2-ethyl-4,4-dimethyl-3,4-dihydro-2H-isoquinolin-1-one (17 mg, 0.05 mmol) and pyridine (9 µl, 0.11 mmol) in anhydrous acetonitrile (1 ml) was added 1-methyl-1H-imidazole-4-sulfonyl chloride (20 mg, 0.11 mmol) and the reaction heated to 150° C. in a microwave for 0.5 hrs. The solvent was evaporated in vacuo and the crude residue purified by preparative tlc (5% methanol in dichloromethane) to afford the title compound as a colourless solid (5 mg, 21%). HPLC retention time 4.42 min. Mass spectrum (ES+) m/z 487 (M+H).

Example 6

1-Methyl-1H-imidazole-4-sulfonic acid (4-chloro-benzyl)-(4,4-dimethyl-1-oxo-1,2,3,4-tetrahydro-isoquinolin-7-yl)-amide (METHOD E)

i) 2-(4-methoxy-benzyl)-4,4-dimethyl-7-nitro-3,4-dihydro-2H-isoquinolin-1-one this compound was prepared according to step iii in example 4 (method D)

ii) 4,4-Dimethyl-7-nitro-3,4-dihydro-2H-isoquinolin-1-one

A solution of 2-(4-methoxy-benzyl)-4,4-dimethyl-7-nitro-3,4-dihydro-2H-isoquinolin-1-one (1.2 g, 3.52 mmol) and cerium ammonium nitrate (5.78 g, 10.56 mmol) in acetonitrile (30 ml) and water (15 ml) was stirred at 0° C. for 1 hrs, after this time the reaction was warmed to room temperature and stirred for a further 15 h. The solvent was evaporated in vacuo and dichloromethane added. The organic phase was separated, washed with saturated aqueous ammonium chloride solution and brine, then dried and evaporated in vacuo. The crude residue was purified by flash column chromatography (15% ethyl acetate in dichloromethane) to afford the title compound (300 mg, 39%). HPLC retention time 3.71 min. Mass spectrum (ES+) m/z 221 (M+H).

iv) 7-Amino-4,4-dimethyl-3,4-dihydro-2H-isoquinolin-1-one

Palladium/Carbon (10% wt) (25 mg, 0.13 mmol) was added to a stirred solution of 4,4-dimethyl-7-nitro-3,4-dihydro-2H-isoquinolin-1-one (250 mg, 1.13 mmol) and ammonium formate (350 mg, 5.65 mmol) in anhydrous DMF (10 ml) at room temperature. The resulting suspension was then heated at reflux for 1 hrs, then cooled and filtered through a pad of celite. The solvent was evaporated and the crude residue purified by flash column chromatography (5% methanol in dichloromethane) to afford the title compound as a pale yellow solid (210 mg, 98%). HPLC retention time 1.00 min. Mass spectrum (ES+) m/z 191 (M+H).

v) 7-(4-Chloro-benzylamino)-4,4-dimethyl-3,4-dihydro-2H-isoquinolin-1-one

Sodium triacetoxyborohydride (800 mg, 3.79 mmol) was added to a stirred solution of 7-amino-4,4-dimethyl-3,4-dihydro-2H-isoquinolin-1-one (220 mg, 1.15 mmol), 4-chlorobenzaldehyde (324 mg, 2.31 mmol) and acetic acid (69 µl, 1.15 mmol) in anhydrous dichloromethane (10 ml) at room temperature. The reaction was stirred overnight and quenched with the addition of water. The organic phase was separated, washed with brine, then dried (MgSO$_4$) and evaporated in vacuo. The resulting residue was purified by flash column chromatography (20% ethyl acetate in dichloromethane) to afford the title compound as a light brown solid (140 mg, 39%). HPLC retention time 4.40 min. Mass spectrum (ES+) m/z 315 (M+H).

vi) 1-Methyl-1H-imidazole-4-sulfonic acid (4-chloro-benzyl)-(4,4-dimethyl-1-oxo-1,2,3,4-tetrahydro-isoquinolin-7-yl)-amide To a stirred solution of 7-(4-chloro-benzylamino)-4,4-dimethyl-3,4-dihydro-2H-isoquinolin-1-one (20 mg, 0.06 mmol) and pyridine (12 µl, 0.14 mmol) in anhydrous acetonitrile (1 ml) was added 1-methyl-1H-imidazole-4-sulfonyl chloride (25 mg, 0.14 mmol) and the reaction heated to 150° C. in a microwave for 0.5 hrs. The solvent was evaporated in vacuo and the crude residue purified by preparative HPLC (Method A) to afford the title compound as a colourless solid (15 mg, 21%). HPLC retention time 4.07 min. Mass spectrum (ES+) m/z 459 (M+H).

Other compounds prepared by Method E as described for example 6 using the appropriate starting materials are listed in TABLE 1

Example 7

1-Methyl-1H-imidazole-4-sulfonic acid (4-chloro-benzyl)-(2-isopropyl-1,3-dioxo-2,3-dihydro-1-H-isoindol-5-yl)-amide (METHOD F)

i) 2-Isopropyl-5-nitro-isoindole-1,3-dione

To a stirred solution of 4-nitrophthalimide (2.0 g, 10.41 mmol), triphenylphosphine (11.45 mmol, 2.99 g) and isopropanol (11.45 mmol, 0.73 ml) in anhydrous THF (40 ml) was added diisopropylazodicarboxylate (2.37 g, 11.45 mmol) and the reaction stirred for 16 hrs at room temperature. Water and ethyl acetate were added and the organic phase separated, washed with brine, then dried (MgSO$_4$) and evaporated in vacuo. The crude residue was purified by flash column chromatography (30% ethyl acetate in petroleum ether) to afford the title compound as a pale yellow solid (1.27 g, 52%). HPLC retention time 4.60 min. Mass spectrum (ES+) m/z 235 (M+H).

ii) 5-Amino-2-isopropyl-isoindole-1,3-dione

A solution of sodium borohydride (193 mg, 5.12 mmol) in ethanol (4 ml) was added dropwise to a stirred solution of 2-isopropyl-5-nitro-isoindole-1,3-dione (1.20 g, 5.12 mmol) and tin (II) dichloride dihydrate (3.47 g, 15.36 mmol) in ethanol (40 ml) at 60° C. The resulting solution was stirred for 2 hrs, after which time the reaction was cooled to 0° C. and basified using 2M sodium hydroxide. The aqueous phase was extracted with dichloromethane (3×20 ml) and the combined organics washed with brine, then dried (MgSO$_4$) and evaporated in vacuo. The crude residue was purified by preparative HPLC (Method D) to afford the title compound as a yellow solid (512 mg, 49%). HPLC retention time 7.2 min. Mass spectrum (ES+) m/z 205 (M+H).

iii) 5-(4-Chloro-benzylamino)-2-isopropyl-isoindole-1,3-dione

Sodium triacetoxyborohydride (1.03 g, 4.90 mmol) was added to a stirred solution of 5-amino-2-isopropyl-isoindole-1,3-dione (0.50 g, 2.69 mmol), 4-chlorobenzaldehyde (0.37 g, 2.69 mmol), and acetic acid (160 μl, 2.69 mmol) in anhydrous dichloromethane (10 ml) at room temperature. The reaction was stirred overnight and quenched with the addition of water. The organic phase was separated, washed with brine, then dried (MgSO$_4$) and evaporated in vacuo. The resulting residue was purified by flash column chromatography (5% methanol in dichloromethane) to afford the title compound as a light brown solid (160 mg, 20%). HPLC retention time 4.86 min. Mass spectrum (ES+) m/z 329 (M+H).

iv) 1-Methyl-1H-imidazole-4-sulfonic acid (4-chloro-benzyl)-(2-isopropyl-1,3-dioxo-2,3-dihydro-1-H-isoindol-5-yl)-amide To a stirred solution of 5-(4-chloro-benzylamino)-2-isopropyl-isoindole-1,3-dione (50 mg, 0.15 mmol) and pyridine (36 μl, 0.45 mmol) in anhydrous dichloromethane (2 ml) was added 1-methyl-1H-imidazole-4-sulphonyl chloride (60 mg, 0.27 mmol) and the reaction heated at reflux for 15 hrs. The reaction was cooled and the solvent evaporated in vacuo. The crude residue was purified by preparative HPLC (Method D) to afford the title compound as a colourless solid (5 mg, 7%). HPLC retention time 8.14 min. Mass spectrum (ES+) m/z 473 (M+H).

TABLE 1

Summary of synthesis methods, characterisation data and biological activity

| Example Number | Compound Name | Method | LCMS Ret.n time | (ES+) m/z (M + H) | hK$_v$1.3 % inh. 1 uM | hK$_v$1.5 % inh. 300 nM |
|---|---|---|---|---|---|---|
| 1 | 1-Methyl-1H-pyrazole-3-sulfonic acid (4-chloro-benzyl)-(2-ethyl-1-oxo-1,2,3,4-tetrahydro-isoquinolin-7-yl)-amide | C | 4.34 | 459 | 99.6 | 82.4 |
| 2 | Pyridine-3-sulfonic acid (40chloro-benzyl)-(2-ethyl-3-oxo-2,3-dihydro-1H-isoindol-5-yl)-amide | B | 4.28 | 442 | 97.2 | 65.0 |
| 3 | N-(4-Chloro-benzyl)-3-cyano-N-(1-oxo-1,2,3,4-tetrahydro-isoquinolin-7-yl)-benzenesulfonamide | C | 4.28 | 497 | 97.2 | 87.8 |
| 4 | 1-Methyl-1H-pyrazole-3-sulfonic acid (4-chloro-benzyl)-(2-ethyl-3-oxo-2,3-dihydro-1H-isoindol-5-yl)-amide | B | 4.27 | 445 | 96.6 | 63.8 |
| 5 | Pyridine-3-sulfonic acid (4-chloro-benzyl)-[2-(2-hydroxy-ethyl)-1-oxo-1,2,3,4-tetrahydro-isoquinolin-7-yl]-amide | C | 4 | 473 | 96.4 | 76.0 |
| 6 | 1-Methyl-1H-imidazole-4-sulfonic acid (4-chloro-benzyl)-(2-ethyl-4,4-dimethyl-1-oxo-1,2,3,4-tetrahydro-isoquinolin-7-yl)-amide | E | 4.42 | 487 | 96.1 | 70.1 |
| 7 | 1-Methyl-1H-pyrazole-3-sulfonic acid (4-chloro-benzyl)-(1-oxo-1,2,3,4-tetrahydro-isoquinolin-7-yl)-amide | C | 4.08 | 432 | 95.5 | 42.6 |
| 8 | N-(4-Chloro-benzyl)-3-cyano-N-(1-oxo-1,2,3,4-tetrahydro-isoquinolin-7-yl)-benzenesulfonamide | C | 2.9 | 452 | 94.6 | 91.2 |
| 9 | 1-Methyl-1H-pyrazole-3-sulfonic acid (4-chloro-benzyl)-(2-methyl-1-oxo-1,2,3,4-tetrahydro-isoquinolin-7-yl)-amide | C | 4.28 | 445 | 94.5 | 76.4 |
| 10 | 1-Methyl-1H-pyrazole-3-sulfonic acid (4-chloro-benzyl)-[2-(2-hydroxy-ethyl)-1-oxo-1,2,3,4-tetrahydro-isoquinolin-7-yl]-amide | C | 3.98 | 476 | 94.2 | 47.1 |
| 11 | N-(4-Chloro-benzyl)-3-cyano-n-(2-ethyl-3-oxo-2,3-dihydro-1H-isoindol-5-yl)-benzene | B | 4.53 | 466 | 93.8 | 86.9 |

TABLE 1-continued

Summary of synthesis methods, characterisation data and biological activity

| Example Number | Compound Name | Method | LCMS Ret.n time | (ES+) m/z (M + H) | hK$_v$1.3 % inh. 1 uM | hK$_v$1.5 % inh. 300 nM |
|---|---|---|---|---|---|---|
| 12 | N-(4-Chloro-benzyl)-3-cyano-N-(2-ethyl-1-oxo-2,3-dihydro-1H-isoindol-5-yl) benzene sulfonamide | B | 4.49 | 466 | 93.0 | 63.2 |
| 13 | Pyridine-3-sulfonic acid (4-chloro-benzyl)-(1-oxo-1,2,3,4-tetrahydro-isoquinolin-7-yl)-amide | C | 2.59 | 428 | 90.5 | 36.0 |
| 14 | 1-Methyl-1H-imidazole-4-sulfonic acid (4-chloro-benzyl)-(2-ethyl-3-oxo-2,3-dihydro-1H-isoindol-5-yl)-amide | B | 4.04 | 445 | 89.7 | 27.1 |
| 15 | Pyridine-3-sulfonic acid 94-chloro-benzyl)-(4,4-dimethyl-1-oxo-1,2,3,4-tetrahydro-isoquinolin-7-yl)-amide | F | 4.29 | 456 | 88.9 | 70.0 |
| 16 | 1-Methyl-1H-pyrazole-3-sulfonic acid (4-chloro-benzyl)-(4,4-dimethyl-1-oxo-1,2,3,4-tetrahydro-isoquinolin-7-yl)-amide | F | 4.27 | 459 | 88.3 | 64.2 |
| 17 | 1-Methyl-1H-imidazole-4-sulfonic acid (4-chloro-benzyl)-(2-isopropyl-1,3-dioxo-2,3-dihydro-1-H-isoindol-5-yl)-amide | G | 8.14 | 473 | 79.7 | 58.0 |
| 18 | 1-Methyl-1H-pyrazole-3-sulfonic acid (4-chloro-benzyl)-(2-ethyl-1-oxo-2,3-dihydro-1H-isoindol-5-yl)-amide | B | 4.18 | 445 | 75.2 | 77.3 |
| 19 | 1-Methyl-1H-pyrazole-3-sulfonic acid benzyl (2-ethyl-1-oxo-1,2,3,4-tetrahydro-isoquinolin-6-yl)-amide | D | 4.14 | 425 | 74.3 | 25.4 |
| 20 | 1-Methyl-1H-imidazole-4-sulfonic acid (4-chloro-benzyl)-(4,4-dimethyl-1-oxo-1,2,3,4-tetrahydro-isoquinolin-7-yl)-amide | F | 4.07 | 459 | 72.6 | 34.06 |
| 21 | 1-Methyl-1H-imidazole-4-sulfonic acid (4-chloro-benzyl)-(2-ethyl-1-oxo-2,3-dihydro-1H-isoindol-4-yl)-amide | B | 4.02 | 446 | 69.8 | 23.8 |
| 22 | 1-Methyl-1H-imidazole-4-sulfonic acid (4-chloro-benzyl)-(2-ethyl-1-oxo-2,3-dihydro-1H-isoindol-5-yl)-amide | B | 4 | 445 | 67.9 | 30.6 |
| 23 | 1-Methyl-1H-imidazole-4-sulfonic acid benzyl-(2-ethyl-1-oxo-1,2,3,4-tetrahydro-isoquinolin-6-yl)-amide | D | 3.91 | 425 | 58.0 | 26.5 |

REFERENCES

Herbert, "General principles of the structure of ion channels", Am. J. Med, 104, 87-98, 1998.

Armstrong & Hille, "Voltage-gated ion channels and electrical excitability", Neuron, 20, 371-380, 1998.

Gutman G A et al., "International Union of Pharmacology. XLI. Compendium of voltage-gated ion channels: potassium channels". Pharmacol Rev. December; 55(4):583-6, 2003.

Shieh et al., "Potassium Channels: Molecular Defects, Diseases, and Therapeutic Opportunities", Pharmacol Rev, 52(4), 557-594, 2000.

Ford et al., "Potassium Channels: Gene Family, Therapeutic Relevance, High-Throughput Screening Technologies and Drug Discovery", Prog Drug Res, 58, 133-168, 2002.

Xie M et al., "Ion Channel Drug Discovery Expands into New Disease Areas", Current Drug Discovery, 31-33, 2004.

Cahalan M D & Chandy K G, "Ion Channels in the Immune System as Targets for Immunosuppression", Current Opinion in Biotechnology, 8, 749-756, 1997.

Beeton et al., "Kv1.3 channels are a therapeutic target for T cell-mediated autoimmune diseases", Proceeds of the National Academy of Sciences, 46, 103, 17414-17419, 2006

Wulff H, Beeton C, Chandy K G: Potassium channels as therapeutic targets for autoimmune disorders. (2003) *Curr. Opin. Drug Dis.* 6(5):640-647

Beeton C, Pennington M W, Wulff H, Singh S, Nugent D, Crossley G, Khaytin I, Calabresi P A, Chen C Y, Gutman G A, Chandy K G. Targeting effector memory T cells with a selective peptide inhibitor of Kv1.3 channels for therapy of autoimmune diseases. (2005) *Mol Pharmacol.* 67(4):1369-81.

Panyi G, Varga Z, Gaspar R. Abstract Ion channels and lymphocyte activation. (2004) *Immunology Lett.* 92:55-66.

Chandy K G, Wulff H, Beeton C, Pennington M, Gutman G, Cahalan M: K+ channels as targets for specific immunomodulation. *TIPS.* (2004) 25(5):280-289

Beeton C, Barbaria J, Giraud P, Devaux J, Benoliel A, Gola M, Sabatier J M, Bernard D, Crest M, Beraud E: Selective blocking of voltage-gated K+ channel improves experimental autoimmune encephalomyelitis and inhibits T cell activation. (2001) *J. Immunol.* 166:936-944

Price M J, Lee S C, Deutsch C: Charybdotoxin inhibits proliferation and interleukin-2 production of human peripheral blood lymphocytes. (1989) *Proc. Natl. Acad. Sci.* 86:10171-10175

Koo G C, Blake J T, Shah K, Staruch M J, Dumont F, Wunderler D L, Sanchez M, McManus O B, Sirontina-Meisher A, Fischer P, Boltz R C, Goetz M A, Baker R, Bao J, Kayser F, Rupprecht K M, Parsons W H, Tong X, Ita I E, Pivnichny J, Vincent S, Cunningham P, Hora D, Feeney W, Kaczorowski G, Springer M S: Correolide and derivatives are novel immunosuppressants blocking the lymphocyte Kv1.3 potassium channels. (1999) *Cell. Immunol.,* 197:99-107

Schmitz A, Sankaranarayanan A, Azam P, Schmidt-Lassen K, Homerick D, Hansel W, Wulff H: Design of PAP-1, a selective small molecule Kv1.3 blocker, for the suppression of effector memory cells in autoimmune diseases. (2005) Mol. Pharmacol., 68:1254-1270

Triggle D. J, Gopalakkrishnan M, Rampe D, Zheng W: Voltage gated Ion channels as Drug Targets, Wiley, 2005)

Sands et al,: Charabydotoxin blocks voltage-gated K+ channels in human and murine T lymphocytes. J. Gen-Physiol. 1989, 93, 10061-1074.

Garcia et al, Purification, characterisation and biosynthesis of margatoxin, a component of Centruroides maragritatus venom that selectively inhibits voltage-gated potassium channels, J. Biol. Chem. 1993, 268, 18866-1887

Garcia et al,: Purification and characterisation of three inhibitors of voltage dependent K+ channels from Leiurus quinquesttriatus var. hebraeus. Biochemistry, 1994, 33, 6834-6839

Koshchak et al., Subunit composition of brain voltage-gated potassium channels determined by hongotoxin-1, a novel peptide derived from Centruroides limbatus venom. J. Biol. Chem. 1998, 273, 2639-2644.

Peter et al, Effect of toxins Pi2 and Pi3 on human T Lymphocyte kv1.3 channels: the role of Glu7 and Lys24. J. Membr. Biol. 2001, 179, 13-25

Mouhat et al, K+ channel types targeted by synthetic OSK1, a toxin from Orthochirus scrobiculosus scorpion venom Biochem. J. 2005, 385, 95-104

Pennington et al, Identification of there separate binding sites on Shk toxin, a potent inhibitor of voltage dependent potassium channels in human T-lymphocytes and rat brain. Biochem. Biophys. Res. Commun. 1996, 219, 696-701

Pennington et al, ShK-Dap[22], a potent Kv1.3-specific immunosuppressive polypeptide. J. Biol. Chem. 1998, 273, 32697-35707

Nguyen A et al., "Novel Nonpeptide Agents Potently Block the C-Type Inactivated Conformation of Kv1.3 and Suppress T Cell Activation", Mol. Pharmacol., 50, 1672-1679, 1996.

Hanson D C et al., "UK-78,282, a Novel Piperidine Compound That Potently Blocks the Kv1.3 Voltage-Gated Potassium Channel and Inhibits Human T Cell Activation", Br. J. Pharmacol., 126, 1707-1716, 1999.

Felix J P et al., "Identification and Biochemical Characterization of a Novel Norterpene Inhibitor of the Human Lymphocyte Voltage-Gated Potassium Channel, Kv1.3", Biochemistry, 38 (16), 4922-4930, 1999.

Baell J B et al., "Khellinone Derivatives as Blockers of the Voltage-Gated Potassium Channel Kv1.3: Synthesis and Immunosuppressive Activity" J. Med. Chem., 47, 2326-2336, 2004.

Wulff H et al., "Alkoxypsoralens, Novel Nonpeptide Blockers of Shaker-Type K+ Channels: Synthesis and Photoreactivity", J. Med. Chem., 41, 4542-4549, 1998.

Vennekamp J, Wulff H, Beeton C, Calabresi P A, Grissmer S, Hansel W, and Chandy K G. Kv1.3-blocking 5-phenylalkoxypsoralens: a new class of immunomodulators. (2004) *Mol. Pharmacol.* 65, 1364-74.

Marban "Cardiac channelopalthies", Nature, 415, 213-218, 213-218, 2002

Brendel and Peukert 'Blockers of the Kv1.5 Channel for the Treatment of Atrial Arrhythmias', Expert Opinion in Therapeutic Patents, 12 (11), 1589-1598 (2002).

What is claimed is:
1. A compound of formula (I):

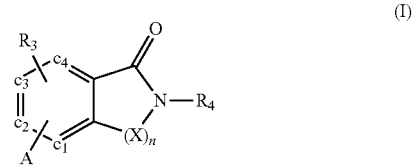

or a pharmaceutically acceptable salt thereof, wherein:
A is a chemical moiety having formula (II):

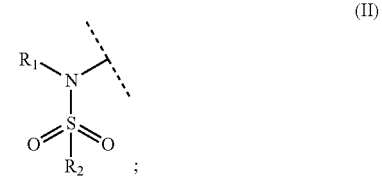

X is selected from the group consisting of $CH_2$, $C(=O)$, $CH(R_5)$, $C(R_5)(R_6)$, and $C(R_5)(R_6)CH_2$;
$R_1$ is selected from the group consisting of optionally substituted arylalkyl and optionally substituted heteroarylalkyl;

$R_2$ is selected from the group consisting of optionally substituted aryl, optionally substituted heteroaryl, and $NR_7R_8$;

$R_3$ is selected from the group consisting of hydrogen, halogen, hydroxyl, alkoxy, aryloxy, optionally substituted alkyl, optionally substituted amino, optionally substituted amino sulfonyl and nitrile;

$R_4$ is selected from the group consisting of hydrogen, optionally substituted alkyl, optionally substituted cycloalkyl, optionally substituted heterocycloalkyl, optionally substituted acyl, optionally substituted sulfonyl, optionally substituted sulfamoyl, optionally substituted aryl, optionally substituted arylalkyl, and optionally substituted heteroaryl;

$R_5$ and $R_6$ for each occurrence is optionally substituted alkyl;

$R_7$ and $R_8$ are the same or different and each represents hydrogen, optionally substituted alkyl, optionally substituted cycloalkyl, optionally substituted arylalkyl, optionally substituted aryl or optionally substituted heteroaryl; and n=1 or 2.

2. A compound according to claim 1, wherein:
the chemical moiety A is attached to the compound of formula (I) via chemical bond at $C_1$, $C_2$ or $C_3$;
X is $CH_2$, $C(\!=\!O)$ or $C(R_5)(R_6)CH_2$; and
n=1 or 2.

3. A compound according to claim 2, wherein:
$R_1$ has the formula (III):

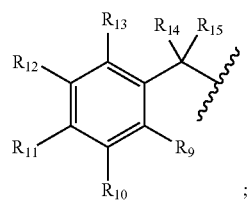

(III)

; and $R_9$, $R_{10}$, $R_{11}$, $R_{12}$ and $R_{13}$ are the same or different and each represents hydrogen, halogen, hydroxyl, optionally substituted amino, optionally substituted acyl, nitrile, optionally substituted $C_{1-3}$ alkyl or optionally substituted alkoxy;

$R_{14}$ and $R_{15}$ are the same or different and each represents hydrogen, hydroxyl, or optionally substituted $C_{1-3}$ alkyl.

4. A compound according to claim 2, wherein:
$R_2$ is formula (IV), (V) or (VI):

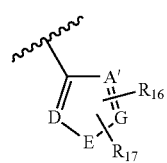

(IV)

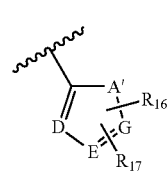

(V)

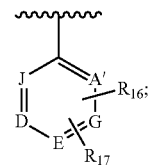

(VI)

A', D, E, G, and J are the same or different and each represents C or N, with the proviso that in each instance at least one of A, D, E, G, or J is N; and When $R_2$ is formula (IV), E may also represent O or S; and When $R_2$ is formula (V), A may also represent O or S; and $R_{16}$ and $R_{17}$ are the same or different and each represents hydrogen, halogen, hydroxyl, nitrile, optionally substituted amino, optionally substituted acyl, optionally substituted $C_{1-3}$ alkyl, optionally substituted arylalkyl, optionally substituted aryl or optionally substituted heteroaryl, or $R_{16}$ and $R_{17}$ may be taken together to form an optionally substituted saturated or partially saturated 5-7 membered heterocyclic or carbocyclic ring.

5. A compound according to claim 2, wherein $R_2$ is formula (VII)

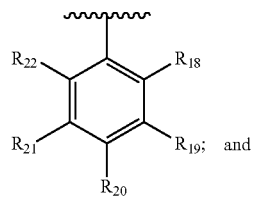

(VII)

$R_{18}$, $R_{19}$, $R_{20}$, $R_{21}$, and $R_{22}$ are the same or different and each represents hydrogen, halogen, hydroxyl, optionally substituted amino, optionally substituted acyl, nitrile, or optionally substituted $C_{1-3}$ alkyl, or any of the pairs $R_{18}$ and $R_{19}$, or $R_{19}$ and $R_{20}$, or $R_{20}$ and $R_{21}$, or $R_{21}$ and $R_{22}$ may be taken together to form an optionally substituted saturated or partially saturated 5-7 membered heterocyclic or carbocyclic ring.

6. A compound according to claim 2, wherein
$R_3$ is H, F or $CH_3$.

7. A compound according to claim 2, wherein
$R_4$ is preferably selected from the group consisting of hydrogen, optionally substituted alkyl, optionally substituted cycloalkyl, optionally substituted heterocycloalkyl, optionally substituted acyl, optionally substituted arylalkyl, and optionally substituted heteroaryl.

8. A compound according to claim 2, wherein
$R_5$ and $R_6$ are optionally substituted alkyl.

9. A compound according to claim 2, wherein: A is a chemical moiety of Formula (VIII):

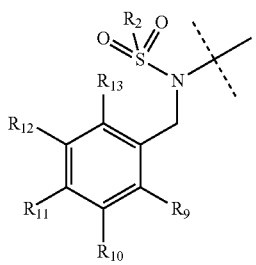

(VIII)

$R_2$ is formula (IV), (V) (VI) or (VII)

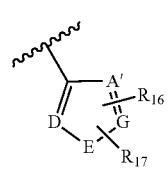

(IV)

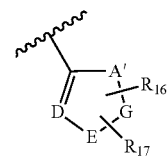

(V)

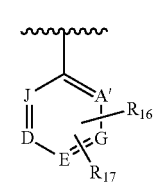

(VI)

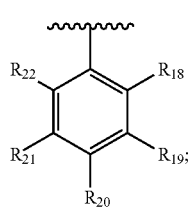

(VII)

A', D, E, G, and J are the same or different and each represents C or N, with the proviso that in each instance at least one of A, D, E, G, or J is N; and When $R_2$ is formula (IV), E may also represent O or S; and When $R_2$ is formula (V), A may also represent O or S;

$R_{16}$ and $R_{17}$ are the same or different and each represents hydrogen, halogen, hydroxyl, nitrile, optionally substituted amino, optionally substituted acyl, optionally substituted $C_{1-3}$alkyl, optionally substituted arylalkyl, optionally substituted aryl or optionally substituted heteroaryl, or $R_{16}$ and $R_{17}$ may be taken together to form an optionally substituted saturated or partially saturated 5-7 membered heterocyclic or carbocyclic ring;

$R_{18}$, $R_{19}$, $R_{20}$, $R_{21}$, and $R_{22}$ are the same or different and each represents hydrogen, halogen, hydroxyl, optionally substituted amino, optionally substituted acyl, nitrile, or optionally substituted $C_{1-3}$alkyl, or any of the pairs $R_{18}$ and $R_{19}$, or $R_{19}$ and $R_{20}$, or $R_{20}$ and $R_{21}$, or $R_{21}$ and $R_{22}$ may be taken together to form an optionally substituted saturated or partially saturated 5-7 membered heterocyclic or carbocyclic ring; and $R_9$, $R_{10}$, $R_{11}$, $R_{12}$ and $R_{13}$ are the same or different and each represents hydrogen, halogen, hydroxyl, optionally substituted amino, optionally substituted acyl, nitrile, optionally substituted $C_{1-3}$ alkyl or optionally substituted alkoxy.

10. A compound according to claim 9, wherein: formula (I) is represented by formula (IX), (X), or (XII):

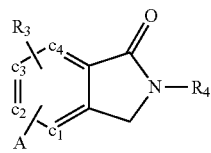

(IX)

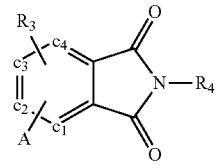

(X)

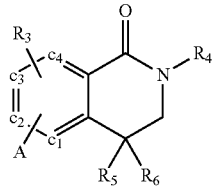

(XI)

$R_3$ is H, F or $CH_3$; and $R_4$ is selected from the growl consisting of hydrogen, optionally substituted alkyl, optionally substituted cycloalkyl, optionally substituted heterocycloalkyl, optionally substituted acyl, optionally substituted arylalkyl, and optionally substituted heteroaryl.

11. A compound according to claim 1 selected from the group consisting of:
1-Methyl-1H-pyrazole-3-sulfonic acid (4-chloro-benzyl)-(2-ethyl-1-oxo-1,2,3,4-tetrahydro-isoquinolin-7-yl)-amide;
Pyridine-3-sulfonic acid (4-chloro-benzyl)-(2 ethyl-3-oxo-2,3-dihydro-1H-isoindol-5-yl)-amide;
N-(4-Chloro-benzyl)-3-cyano-N-(1-oxo-1,2,3,4-tetrahydro-isoquinolin-7-yl)-benzenesulfonamide;
1-Methyl-1H-pyrazole-3-sulfonic acid (4-chloro-benzyl)-(2-ethyl-3-oxo-2,3-dihydro-1H-isoindol-5-yl)-amide;
Pyridine-3-sulfonic acid (4-chloro-benzyl)-[2-(2-hydroxy-ethyl)-1-oxo-1,2,3,4-tetrahydro-isoquinolin-7-yl]-amide;
1-Methyl-1H-imidazole-4-sulfonic acid (4-chloro-benzyl)-(2-ethyl-4,4-dimethyl-1-oxo-1,2,3,4-tetrahydro-isoquinolin-7-yl)-amide;
1-Methyl-1H-pyrazole-3-sulfonic acid (4-chloro-benzyl)-(1-oxo-1,2,3,4-tetrahydro-isoquinolin-7-yl)-amide;
N-(4-Chloro-benzyl)-3-cyano-N-(1-oxo-1,2,3,4-tetrahydro-isoquinolin-7-yl)-benzenesulfonamide;
1-Methyl-1H-pyrazole-3-sulfonic acid (4-chloro-benzyl)-(2-methyl-1-oxo-1,2,3,4-tetrahydro-isoquinolin-7-yl)-amide;
1-Methyl-1H-pyrazole-3-sulfonic acid (4-chloro-benzyl)-[2-(2-hydroxy-ethyl)-1-oxo-1,2,3,4-tetrahydro-isoquinolin-7-yl]-amide;
N-(4-Chloro-benzyl)-3-cyano-n-(2-ethyl-3-oxo-2,3-dihydro-1H-isoindol-5-yl)-benzene sulfonamide;

N-(4-Chloro-benzyl)-3-cyano-N-(2-ethyl-1-oxo-2,3-dihydro-1H-isoindol-5-yl)benzene sulfonamide;
Pyridine-3-sulfonic acid (4-chloro-benzyl)-(1-oxo-1,2,3,4-tetrahydro-isoquinolin-7-yl)-amide;
1-Methyl-1H-imidazole-4-sulfonic acid (4-chloro-benzyl)-(2-ethyl-3-oxo-2,3-dihydro-1H-isoindol-5-yl)-amide;
Pyridine-3-sulfonic acid 94-chloro-benzyl)-(4,4-dimethyl-1-oxo-1,2,3,4-tetrahydro-isoquinolin-7-yl)-amide;
1-Methyl-1H-pyrazole-3-sulfonic acid (4-chloro-benzyl)-(4,4-dimethyl-1-oxo-1,2,3,4-tetrahydro-isoquinolin-7-yl)-amide;
1-Methyl-1H-imidazole-4-sulfonic acid (4-chloro-benzyl)-(2-isopropyl-1,3-dioxo-2,3-dihydro-1-H-isoindol-5-yl)-amide;
1-Methyl-1H-pyrazole-3-sulfonic acid (4-chloro-benzyl)-(2-ethyl-1-oxo-2,3-dihydro-1H-isoindol-5-yl)-amide;
1-Methyl-1H-pyrazole-3-sulfonic acid benzyl (2-ethyl-1-oxo-1,2,3,4-tetrahydro-isoquinolin-6-yl)-amide;
1-Methyl-1H-imidazole-4-sulfonic acid (4-chloro-benzyl)-(4,4-dimethyl-1-oxo-1,2,3,4-tetrahydro-isoquinolin-7-yl)-amide;
1-Methyl-1H-imidazole-4-sulfonic acid (4-chloro-benzyl)-(2-ethyl-1-oxo-2,3-dihydro-1H-isoindol-4-yl)-amide;
1-Methyl-1H-imidazole-4-sulfonic acid (4-chloro-benzyl)-(2-ethyl-1-oxo-2,3-dihydro-1H-isoindol-5-yl)-amide; and
1-Methyl-1H-imidazole-4-sulfonic acid benzyl-(2-ethyl-1-oxo-1,2,3,4-tetrahydro-isoquinolin-6-yl)-amide.

12. The compound of claim 2, wherein n is 1 or 2 when X is $CH_2$, and n is 1 when X is C(=O).

13. The compound of claim 3, wherein $R_{10}$, $R_{11}$, and $R_{12}$ are the same or different and each represents H, Cl, F, or $CH_3$.

14. The compound of claim 4, wherein $R_2$ is selected from the group consisting of imidazole, pyrazole, pyrrole, oxazole, oxadiazole, thiazole, thiadiazole, pyridine, pyrimidine, pyrazine, pyridazine, and triazine.

15. The compound of claim 14, wherein $R_2$ is selected from the group consisting of imidazole, pyrazole, and pyridine.

16. The compound of claim 4, wherein $R_{16}$ and $R_{17}$ are alkyl.

17. The compound of claim 16, wherein, $R_{16}$ and $R_{17}$ are $CH_3$.

18. The compound of claim 5, wherein $R_2$ is selected from the group consisting of phenyl, fluorophenyl, cyanophenyl, tetrahydrobenzofuran, benzopyran, dihydrobenzodioxin, benzoxazinone, benzooxadiazole, benzodioxole, indoline, and benzomorpholine.

19. The compound of claim 6, wherein $R_3$ is H or F.

20. The compound of claim 7, wherein $R_4$ is selected from the group consisting of hydrogen, methyl, ethyl, propyl, isopropyl and 2-hydroxyethyl.

21. The compound of claim 8, wherein $R_5$ and $R_6$ are $CH_3$.

22. A pharmaceutical composition comprising at least one compound as claimed in claim 1 or 11 together with one or more pharmaceutically acceptable excipients, diluents and/or carriers.

23. A method for the treatment of arrhythmia, psoriasis, rheumatoid arthritis, multiple sclerosis, type 1 diabetes, type-2 diabetes mellitus, or inflammatory bowel disorder, comprising administering to a subject an effective amount of a compound of claim 1 or 11, or a pharmaceutically acceptable salt thereof.

24. A method as claimed in claim 23, wherein the disorder is arrhythmia.

25. A method as claimed in claim 23, wherein the disorder is psoriasis, rheumatoid arthritis, or multiple sclerosis.

* * * * *